United States Patent [19]

Nagai et al.

[11] 4,421,761
[45] Dec. 20, 1983

[54] THIOPHENE DERIVATIVES

[75] Inventors: Shigeki Nagai, Hirota; Yojiro; Takashi Yorie; Hisao Sugiura; Toru Hibi, all of Ube; Katsumi Sato, Hiratsuka; Takuo Wada, Hatano; Masahiko Miyahara, Atsugi, all of Japan

[73] Assignees: Hokko Chemical Industry Co. Ltd.; Ube Industries, Ltd., both of Japan

[21] Appl. No.: 228,696

[22] Filed: Jan. 27, 1981

[51] Int. Cl.³ .................... A01N 43/02; C07D 333/24
[52] U.S. Cl. ................................. 424/275; 424/200; 424/202; 424/263; 424/267; 424/274; 549/59; 549/60; 549/61; 549/62; 549/64; 549/65; 549/66; 549/8; 546/193; 546/212; 546/268; 548/527; 260/239 BF
[58] Field of Search .................... 546/193, 212, 268; 548/527; 549/64, 8, 59, 60, 61, 62, 65, 66; 424/275, 200, 202, 263, 267, 274; 260/239 BF

[56] References Cited

U.S. PATENT DOCUMENTS 2,453,102 11/1948 Turnbull .............................. 549/64

Primary Examiner—Alan Siegel
Attorney, Agent, or Firm—Abelman, Frayne & Rezac

[57] ABSTRACT

Thiophene derivatives of the formula

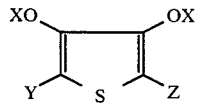

wherein X, Y and Z are as herein defined, said compounds being useful as fungicides, are described.

12 Claims, No Drawings

THIOPHENE DERIVATIVES

This invention relates to novel thiophene derivatives and to fungicides for agricultural and horticultural purposes which are characterized by containing as their active ingredients said derivatives. The novel thiophene derivatives prepared according to the present invention are represented by the general formula (I)

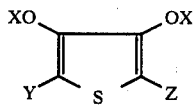

wherein X represents hydrogen atom, alkali metal, $NH_4$, $COR_1$ (in which $R_1$ represents phenyl, halophenyl, lower alkyl, lower alkenyl, lower alkoxy lower alkyl, lower alkylthio lower alkyl, lower haloalkyl,

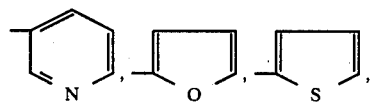

cycloalkyl or lower alkylthio), —CO-lower alkyl-$R_2$ (in which $R_2$ represents lower alkylcarbonyloxy or lower alkoxycarbonyl),

(in which n represents an integer of 4 to 6 inclusive), di-lower alkylcarbamoyl, mono-lower alkylcarbamoyl, cycloalkylcarbamoyl, —$COOR_3$ (in which $R_3$ represents lower alkyl, lower alkenyl, lower alkynyl, lower haloalkyl, lower alkoxy lower alkyl, lower alkoxycarbonyl lower alkyl, phenyl, substituted phenyl or benzyl), —$SO_2R_4$ (in which $R_4$ represents lower alkyl, lower alkyl-substituted phenyl or di-lower alkylamino) or

(in which $R_5$ represents lower alkyl); Y represents —$COOR_6$ (in which $R_6$ represents alkyl, lower alkenyl, lower alkynyl, lower alkoxy lower alkyl or benzyl), hydrogen atom or

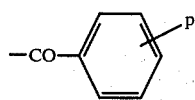

(in which p represents hydrogen atom, halogen atom or lower alkyl); and Z represents $COOR_6$ (in which $R_6$ is as defined above), cyano or

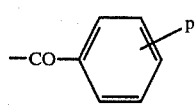

(in which p is as defined above), provided that both Y and Z are not —$COOR_6$ (in which $R_6$ represents alkyl, lower alkenyl or lower alkynyl) when X represents hydrogen atom, alkali metal or $NH_4$.

The term "lower", as used herein in connection with any alkyl, alkenyl or alkynyl portion is to mean that said portion as referred to contains one to four carbon atoms.

A sub-generic group of the particularly useful compounds of the invention can cover the compounds of the general formula (I), wherein X is a group —$COR_1$ (in which $R_1$ is lower alkyl, lower alkoxy lower alkyl, lower alkylthio lower alkyl), a group —$COOR_3$ (in which $R_3$ is lower alkyl) or mono-lower alkylcarbamoyl; Y is a group —$COOR_6$ (in which $R_6$ is lower alkyl, lower alkenyl or lower alkynyl) or a group

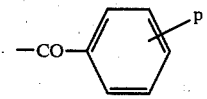

(in which p is hydrogen or halogen); and Z is a group —$COOR_6$ as defined above.

The present inventors prepared by synthesis a large number of thiophene derivatives and extensively studied and invenstigated on practical usefulness of these thiophene derivatives as fungicides for agricultural and horticultural purposes. As a result, it has been found that novel compounds represented by the aforesaid general formula (I) are broadly and divergently usable as fungicides for agricultural and horticultural purposes, exhibiting their controlling activity against various plant deseases such as rice blast, rice brown spot, rice sheath blight, tomato late blight, haricot sclerotinia rot, rice 'Bakanae' disease, cucumber Fusarium wilt, tomato leaf mold, grape ripe rot, pear black spot, Japanese apple canker, vegetable soft rot, rice bacterial blight, cucumber bacterial spot, cucumber downy mildew, cucumber powdery mildew, cucumber anthracnose, etc.

The compounds of the general formula (I) of the present invention can be prepared according to processes represented by the following reaction formulas, respectively.

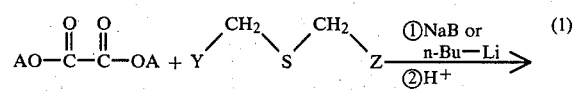

wherein A is alkyl, lower alkenyl, lower alkynyl, lower alkoxy lower alkyl or benzyl; and Y and Z are individually defined as previously.

The instant reaction can be carried out in an organic solvent such as alcohol, ether, hydrocarbon, DMF (dimethylformamide), etc., in the presence of a deprotonating reagent such as metallic sodium, sodium hydride, butyl lithium, alkali metal alcoholate, etc., at a temperature of 0°–100° C. for 2–24 hours. The reaction mixture can be worked up by pouring it into ice water and then acidifying the resulting mixture with hydrochloric acid, sulfuric acid or the like mineral acid, thereby to have the desired 3,4-dihydroxythiophene derivative separated out.

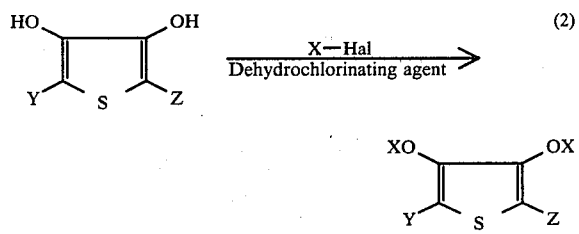

wherein X, Y and Z are individually as defined previously provided that X is not hydrogen, and Hal represents halogen atom.

The above reaction can be carried out in an inert solvent such as dioxane, acetone, benzene, DMF, etc., in the presence of a dehydrohalogenating agent such as triethylamine, pyridine, potassium carbonate, sodium carbonate, etc., at a temperature of 0° to 150° C. for 1-24 hours. After the reaction, the resulting mixture is poured into water and then worked up by filtration, extraction or the like procedures to obtain the intended thiophene derivative.

(2') The compounds of the above formula (I) wherein X is $COR_1$ (in which $R_1$ is lower alkyl) can be prepared by the following reaction:

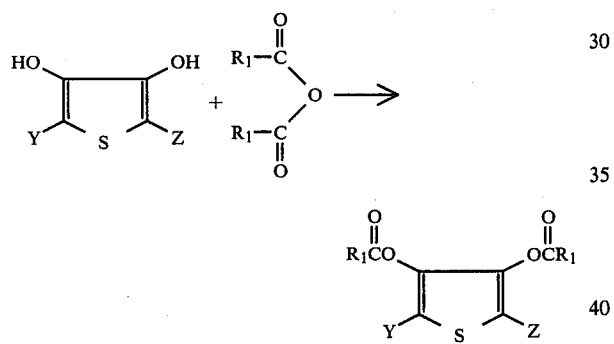

The above reaction can be achieved at a temperature of 30° to 140° C. for 2-16 hours, with or without using a solvent, e.g. benzene, acetic acid, chloroform, ether, etc. by removing an acid formed during the reaction.

(2'') The compounds of the formula (I) wherein X is mono-lower alkylcarbamoyl can be prepared by the following reaction:

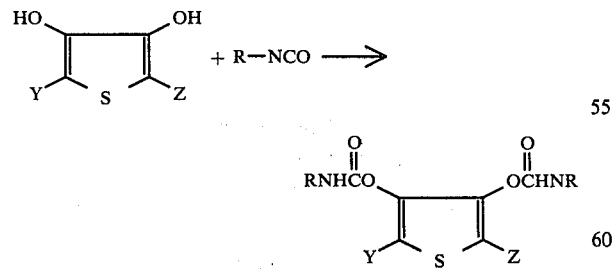

The above reaction is carried out in an inert solvent such as dioxane, benzene, DMF, etc., in the presence of a catalytic amount of triethylamine or the like organic base at a temperature of from room temperature to 80° C. for 2-24 hours. The resulting reaction mixture can be worked up in the similar manner as mentioned above.

Illustrative of the synthesis of the compounds of the present invention are mentioned below with reference to examples.

EXAMPLE 1

3,4-Diacethoxy-2,5-di-n-propoxycarbonylthiopene (Compound No. 3)

A mixture comprising 57.6 g (0.2 mol) of 3,4-dihydroxy-2,5-di-n-propoxycarbonyl-thiophene, 60 ml of acetic anhydride and 1 g of sodium acetate is stirred at about 40° C. to undergo reaction, whereupon the reaction liquid shows pale brown. The reaction is continued at 60°–80° C. for additional 2 hours. Into the reaction liquid having been allowed to cool is poured 500 ml of ice-cooled water, whereby crystals are deposited. The crystal collected by filtration and washed with water are then recrystallized from 60 ml of methanol to give 59 g of the title compound as colorless prisms, m.p. 46°–48° C.

EXAMPLE 2

3,4-Bis(N-methylcarbamoyloxy)-2,5-dicarbethoxy-thiophene (Compound No. 50)

To a solution of 100 g (0.384 mol) of 3,4-dihydroxy-2,5-dicarbethoxy-thiophene in 350 ml of dioxane are added 55 g (0.96 mol) of methyl isocyanate and 10 drops of triethylamine, and the resulting mixture is stirred, whereupon an exothermic reaction occurs and the internal temperature rises to 50°–60° C. The reaction is continued, as it is, for 8 hours (in this case the reaction may be carried out by warming the reaction liquid). After the reaction liquid is allowed to cool, the deposited crystals were collected by filtration and washed with n-hexane, whereupon the title compound is obtained as colorless crystals, m.p. 152°–153° C. The yield 117 g.

EXAMPLE 3

3,4-Dimethoxycarbonyloxy-2,5-dicarbethoxy-thiophene (Compound No. 22)

To a solution of 7.8 g (0.03 mol) of 3,4-dihydroxy-2,5-dicarbethoxy-thiophene in a mixture of 10 g (0.1 mol) of pyridine and 100 ml of benzene is added dropwise while cooling with ice 14.5 g (0.066 mol) of methyl chlorocarbonate in a period of 1.5 hours. The reaction liquid is brought back to room temperature and then stirred for additional 2 hours to terminate the reaction. The reaction liquid is washed with water, dilute solution of sodium hydroxide, dilute hydrochloric acid, and water in that order, dried over sodium sulfate and then concentrated. The concentrate is charged with n-hexane and cooled with ice to deposit crystals. On collecting the deposited crystals by filtration, the title compound is obtained as colorless prisms, m.p. 87°–88° C. The yield 6.5 g.

EXAMPLE 4

3,4-Bis(diethoxythiophophoryloxy)-2,5-dicarbethoxy-thiophene (Compound No. 108)

In a solution of 2.6 g (0.01 mol) of 3,4-dihydroxy-2,5-dicarbethoxy-thiophene in 60 ml of acetone is suspended with stirring 2.8 g (0.02 mol) of sodium carbonate. The suspension was charged with 4.2 g (0.022 mol) of diethyl chlorothiophosphate, and the mixture is heated under reflux for 3 hours. After allowing the reaction liquid to cool, the solvent is distilled off, and the residue is dissolved in benzene. On distilling off the solvent, the title compound is obtained as colorless glass-like flakes, m.p. 105.6° C. The yield 1.7 g.

EXAMPLE 5

3,4-Dihydroxy-2,5-di-2'-ethoxyethoxycarbonylthiophene (Compound No. 159)

Into a mixture of 150 ml of 2-ethoxyethanol and 100 ml of DMF is added with ice-cooling 18 g (0.45 mol) of NaH (60%) powder, and thereto is then added dropwise at room temperature to 80° C. a mixed liquid of 54 g (0.2 mol) of diethoxyethyl ester of thiodiglycolic acid and 63 g (0.3 mol) of diethoxyethyl ester of oxalic acid, followed by stirring at 60°–80° C. for additional 1 hour. The reaction liquid is poured into 50 ml (0.5 mol) of concentrated hydrochloric acid and 500 ml of water, and the deposited crystals are separated by filtration. Recrystallization from aqueous methanol to give 33.2 g (48% yield) as yellow powder, m.p. 79°–80° C.

Elemental analysis (for $C_{14}H_{20}O_8S$): Calculated (%): C 48.27; H 5.79. Found (%): C 50.00; H 5.90.

EXAMPLE 6

3,4-Di-methylcarbamoyloxy-2,5-di-2'-ethoxyethoxycarbonylthiophene (Compound No. 161)

To a solution of 3.5 g (0.01 mol) of 3,4-dihydroxy-2,5-di-2'-ethoxyethoxycarbonylthiophene and 1.2 g (0.02 mol) of methyl isocyanate is added 0.1 ml of triethylamine, and the mixture is stirred at room temperature for 7 hours. The reaction liquid is then poured into 100 ml of water, and the deposited crystals were separated by filtration. Recrystallization from a mixed solvent of n-hexane and benzene gives 2.1 g (46% yield) of the title compound as white needles, m.p. 87.5° C.

Elemental analysis (for $C_{18}H_{26}N_2O_{10}S$): Calculated (%): C 46.75; H 5.63; N 6.06. Found (%): C 46.90; H, 5.65; N 5.70.

EXAMPLE 7

3,4-Di-methoxymethylcarbonyloxy-2,5-di-2'-methoxyethoxycarbonylthiophene (Compound No. 170)

To a solution of 3.2 g (0.01 mol) of 3,4-dihydroxy-2,5-di-2'-methoxyethoxycarbonylthiophene and 3.0 g (0.028 mol) of methoxyacetyl chloride in 50 ml of dioxane is added dropwisw with ice-cooling 10 ml of triethylamine, and the mixture, after being stirred for 30 minutes, is allowed to undergo reaction at room temperature for additional 1 hour. The reaction liquid is poured into 200 ml of water, and the deposited crystals are separated by filtration. Recrystallization from ethanol to give 1.6 g (35% yield) of the title compound as white needles, m.p. 81.2° C.

Elemental analysis (for $C_{18}H_{24}O_{12}S$): Calculated (%): C 46.55; H 5.17. Found (%): C 46.55; H 5.10.

EXAMPLE 8

3,4-Di-methoxycarbonyloxy-2,5-dibenzyloxycarbonylthiophene (Compound No. 179)

To a solution of 3.8 g (0.01 mol) of 3,4-dihydroxy-2,5-di-benzyloxycarbonylthiophene and 2.2 g (0.023 mol) of methyl chloroformate in 20 ml of dioxane is added 5 ml of pyridine, and the mixture is heated with stirring at 60° C. for 2 hours. After completion of the reaction, the reaction liquid is poured into 150 ml of water, and the deposited crystals are separated by filtration. Recrystallization from ethanol gives 3.2 g (64% yield) of the title compound as white plate-like flakes, m.p. 103.4° C.

Elemental analysis (for $C_{24}H_{20}O_{10}S$): Calculated (%): C 57.60; H 4.00. Found (%): C 57.60; H 4.00.

EXAMPLE 9

3,4-Dihydroxy-2-cyano-5-carbethoxythiophene (Compound No. 210)

A solution of 18.5 g (0.126 mol) of ethyl ester of oxalic acid and 20 g (0.126 mol) of ethyl ester of cyanomethylthioglycolic acid in 50 ml of ethanol is maintained on an ice bath at 2° C. Subsequently, to the solution is gradually added dropwise a sodium ethylate solution prepared by treating 7.3 g (0.315 mol) of metallic sodium with 120 ml of dry ethanol, and the mixture is allowed to undergo reaction for 30 minutes. During that period of time, the reaction temperature is maintained at 2°–5° C. After completion of the reaction, the reaction liquid is allowed to stand in a refrigerator for 2 days, whereupon Na salt is deposited as crystals. The crystals collected is dissolved in 50 ml of water and acidified with hydrochloric acid. Recrystallization from acetic acid to give 14.0 g of the title compound as colorless crystals, m.p. 177°–180° C. (decomposition).

Elemental analysis (for $C_8H_7O_4NS$): Calculated (%): C 45.06; H 3.31; N 6.57. Found (%): C 44.80; H 3.26; N 6.51.

| $H^1$—NMR: | δ (ppm) | 1.4 | (C—CH₃) | 3H |
| --- | --- | --- | --- | --- |
| | δ (ppm) | 4.4 | (O—CH₂—) | 2H |
| | δ (ppm) | 11.1 | (—OH) | 2H |

EXAMPLE 10

3,4-Di(N-ethylcarbamoxyloxy)-2-cyano-5-methoxycarbonylthiophene (Compound No. 208)

One (1) drop of triethylamine is added to a solution in 20 ml of DMF of 1 g (0.005 mol) of 3,4-dihydroxy-2-cyano-5-methoxycarbonylthiophene which has been synthesized in the same manner as in Example 1, and thereot is added dropwise at room temperature 1.5 g of (0.02 mol) of ethyl isocyanate and thereby to effect reaction. The reaction system is warmed for 20 minutes to terminate the reaction, and the reaction liquid is poured into water, whereupon crystals are deposited. Recrystallization from ethanol give 0.4 g of the title compound as colorless crystals, m.p. 118°–121° C.

| H'—NMR: | δ (ppm) | 1.2 | (C—CH₃) | 6H |
| --- | --- | --- | --- | --- |
| | δ (ppm) | 3.3 | (N—CH₂—) | 4H |
| | δ (ppm) | 3.9 | (O—CH₃) | 3H |

| δ (ppm) | 5.5 | O<br>‖<br>(C—NH) | 2H |

EXAMPLE 11

3,4-Di-acethoxy-2-cyano-5-carbethoxythiophene (Compound No. 212)

In 10 ml of acetic anhydride, 1.5 g (0.007 mol) of 3,4-dihydroxy-2-cyano-5-carbethoxythiophene is refluxed for 2 hours. After allowing to cool, the reaction liquid is poured into water, whereupon crystals are deposited whieh are then separated by filtration. Recrystallization from ethanol-water to give 1.4 g of the title compound as colorless crystals, m.p. 92°–94° C.

| H'—NMR: | δ (ppm) | 1.3 | (C—CH$_3$) | 3H |
| | δ (ppm) | 2.4 | O<br>‖<br>(C—CH$_3$) | 6H |
| | δ (ppm) | 4.4 | (O—CH$_2$—) | 2H |

EXAMPLE 12

3,4-Di-(ethylcarbonyldioxy)-2-cyano-5-carbethoxythiophene (Compound No. 216)

To a solution in 30 ml of dioxane of 2 g (0.0094 mol) of 3,4-dihydroxy-2-cyano-5-carbethoxythiophene is added 10 ml of pyridine, and thereto is added dropwise with cooling 3.1 g (0.028 mol) of ethyl chloroformate, whereupon pyridine hydrochloride is immediately deposited. The reaction liquid is stirred, as it is, for 2 hours and then allowed to stand overnight.

The reaction liquid is poured into 200 ml of cold water and then acidified with hydrochloric acid, whereupon crystals are desposited which are then separated by filtration. Recrystallization from ethanol-water to give 2.3 of the title compound as colorless needles, m.p. 53°–54° C.

| H'—NMR: | δ (ppm) | 1.3–1.5 | (C—CH$_3$) | 9H |
| | δ (ppm) | 4.3–4.6 | (O—CH$_2$—) | 6H |

EXAMPLE 13

3,4-Dihydroxy-2-carbomethoxy-5-benzoylthiophene (Compound No. 246)

To an ice-cold solution of 130 g (0.30 mol) of normal butyl lithium (a 15% n-hexane solution) in 400 ml of dry ether is added dropwise with stirring a mixed solution of 27 g (0.12 mol) of methyl ester of phenacylthioglycolic acid and 28 g (0.24 mol) of dimethyl oxalate in 50 ml of dry dioxane and 100 ml of dry ether in a period of about 1 hour. After completion of the addition, the reaction liquid is stirred with ice-cooling for additional 1 hour and then brought back to room temperature, followed by standing for one day. The precipitate thus formed is separated by filtration, washed with a small amount of ether and then dissolved in a possible small amount of acetone. The solution is diluted with water to 5 to 6 times, acidified with dilute hydrochloric acid, salted out with sodium chloride and extracted with a mixed solvent of benzene and ethyl acetate. The organic layer formed is dried over anhydrous sodium sulfate and then distilled under reduced pressure to remove the solvent therefrom. The residue obtained is crystallized from a mixed solvent of benzene and n-hexane to obtain 6.2 g (26% yield) of the title compound as yellow fine powder, m.p. 136°–138° C.

| NMR: | δ (ppm) | 8.2–8.4 | Aromatic | 2H |
| | δ (ppm) | 7.7–8.0 | Aromatic | 3H |
| | δ (ppm) | 4.1 | O—CH$_3$ | |
| | δ (ppm) | 9.6 | OH | |
| | δ (ppm) | 12.3 | OH | |

EXAMPLE 14

3,4-Dihydroxy-2-carbethoxy-5-benzoylthiophene (Compound No. 247)

To an ice-cold solution of 53 g (0.13 mol) of normal butyl lithium (a 15% n-hexane solution) in 200 ml of dry ether is gradually added dropwise with stirring a mixed solution of 12 g (0.05 mol) of ethyl ester of phenacylthioglycolic acid and 15 g (0.10 mol) of diethyl oxalate in 50 ml of dry ether in a period of about 1 hour. After completion of the addition, the reaction liquid is stirred with ice-cooling for additional 30 minutes and then brough back to room temperature, followed by standing for one day. The deposited precipitate is separated by filtration, washed with a small amount of ether and then dissolved in a possible small amount of acetone. The solution is diluted with water to 5 to 6 times, acidified with dilute hydrochloric acid, salted out with sodium chloride and extracted with a mixed solvent of benzene and ethyl acetate. The organic layer formed is dried over anhydrous sodium sulfate and then distilled under reduced pressure to remove the solvent therefrom. The residue obtained is crystallized from a mixed solvent of benzene and n-hexane to obtain 3.2 g (23% yield) of the title compound as yellow microcrystals, m.p. 147°–148° C.

| IR (cm$^{-1}$) | °3300 cm$^{-1}$ | Enolic OH |
| | °1680 cm$^{-1}$ | COOEt |
| | °1600 cm$^{-1}$ | ⟨phenyl⟩—C(=O)— |

| NMR: | δ (ppm) | 8.0–8.2 | Aromatic | 2H |
| | δ (ppm) | 7.5–7.9 | Aromatic | 3H |
| | δ (ppm) | 4.4–4.6 | O—CH$_2$— | |
| | δ (ppm) | 1.3–1.6 | C—CH$_3$ | |
| | δ (ppm) | 9.45 | OH | |
| | δ (ppm) | 11.8 | OH | |

EXAMPLE 15

3,4-Dihydroxy-2-benzoylthiophene (Compound No. 250)

To an ice-cold sodium ethoxide solution prepared from 3.8 g (0.17 mol) of metallic sodium and 200 ml of ethanol is added dropwise with stirring in a period of about 1 hour a mixed solution of 13 g (0.055 mol) of ethyl ester of phenacylthioglycolic acid and 16 g (0.11 mol) of diethyl oxalate in 50 ml of ethanol. After completion of the addition, the ice bath is withdrawn and the reaction liquid is stirred at room temperature for 2 hours. Thereafter, the reaction liquid is poured into saline water, acidified with dilute hydrochloric acid and then extracted with a mixed solvent of benzene and ethyl acetate. The organic layer separated is extracted twice with a dilute aqueous sodium hydroxide solution. The alkaline layer thus formed is acidified with dilute hydrochloric acid and extracted with a mixed solvent of benzene and ethyl acetate. The organic layer obtained is dried over anhydrous sodium sulfate and then distilled under reduced pressure to remove the solvent therefrom, and the residue obtained is crystallized from a small amount of a mixed solvent of benzene and n-hexane to obtain 1.0 g (9% yield) of the title compound as brown powder, m.p. 152°–154° C. (decomp.).

| NMR: | δ (ppm) | 8.2–8.3 | Aromatic | 2H |
|---|---|---|---|---|
| | δ (ppm) | 7.5–8.0 | Aromatic | 3H |
| | δ (ppm) | 7.4 | H | |
| | δ (ppm) | 9.5–11.4 | 2OH | |

EXAMPLE 16

3,4-Dihydroxy-2,5-dibenzoylthiophene (Compound No. 265)

To an ice-cold solution of 55 g (0.13 mol) of normal butyl lithium (a 15% n-hexane solution) in 200 ml of dry ether is gradually added dropwise with stirring in a period of about 1 hour a mixed solution of 13.5 g (0.05 mol) of diphenacyl sulfide and 15 g (0.12 mol) of diethyl oxalate in 50 ml of dry ether. After completion of the addition, the reaction liquid is stirred for 30 minutes, brought back to room temperature and allowed to stand overnight. The reaction liquid is charged with 200 ml of n-hexane and thoroughly stirred, and the precipitate deposited is separated by filtration, washed with a small amount of ether and dissolved in a possible small amount of acetone. The solution is diluted to 5 to 6 times with water, acidified with dilute hydrochloric acid, salted out with sodium chloride and extracted with a mixed solvent of benzene and ethyl acetate. The organic layer obtained is then extracted with a dilute aqueous sodium hydroxide solution. The alkaline layer thus obtained is acidified with dilute hydrochloric acid and extracted with a mixed solvent of benzene and ethyl acetate. The organic layer obtained is dried over anhydrous sodium sulfate and then distilled under reduced pressure to remove the solvent therefrom. The residue obtained is crystallized with a small amount of a mixed solvent of benzene and n-hexane to obtain 1.6 g (10% yield) of the title compound as yellow microgranules, m.p. 179°–181° C.

| NMR: | δ (ppm) | 8.2–8.4 | Aromatic | 4H |
|---|---|---|---|---|
| | δ (ppm) | 7.6–8.1 | Aromatic | 6H |
| | δ (ppm) | 12.15 | 2OH | |

EXAMPLE 17

3,4-Diacetoxy-2-carbethoxy-5-benzoylthiophene (Compound No. 249)

To an ice-cold solution of 1.3 g (0.0045 mol) of 3,4-dihydroxy-2-carbethoxy-5-benzoylthiophene in a mixture of 10 ml of pyridine and 20 ml of dioxane is added dropwise with stirring 1.8 g (0.023 mol) of acetyl chloride. The mixture is stirred, as it is, for 30 minutes and thereafter at room temperature for 1 hour. The reaction liquid is poured into ice-cold water and extracted with benzene. The extract is dried over anhydrous sodium sulfate and then distilled under reduced pressure to remove the solvent therefrom. The residue obtained is subjected to silica gel column chromatography with a mixed solvent of benzene and ethyl acetate to give 0.6 g (36% yield) of the title compound as a viscous reddish brown liquid, $n_d^{22}$ 1.5710.

| NMR: | δ (ppm) | 7.8–7.9 | Aromatic | 2H |
|---|---|---|---|---|
| | δ (ppm) | 7.4–7.7 | Aromatic | 3H |
| | δ (ppm) | 4.3–4.5 | O—CH$_2$— | |
| | δ (ppm) | 1.2–1.5 | CH—CH$_3$ | |
| | δ (ppm) | 2.0 | $\overset{\text{C—CH}_3}{\underset{\text{O}}{\|}}$ | |
| | δ (ppm) | 2.3 | $\overset{\text{C—CH}_3}{\underset{\text{O}}{\|}}$ | |

EXAMPLE 18

3,4-Di(methylcarbonyldioxy)-2-carbethoxy-5-benzoylthiophene (Compound No. 252)

To a solution of 0.5 g (0.0017 mol) of 3,4-dihydroxy-2-carbethoxy-5-benzoylthiophene in 20 ml of dioxane is added 0.6 g (0.006 mol) of triethylamine, and the mixture is ice-cooled. To the ice-cooled mixture is added with stirring 0.6 g (0.0063 mol) of methyl chloroformate, and the mixture is stirred, as it is, for 10 minutes and thereafter at room temperature for additional 1 hour. The reaction liquid is then poured into ice-cold water and extracted with chloroform, and the extract is dried over anhydrous sodium sulfate and then distilled under reduced pressure to remove the solvent therefrom. The residue obtained is subjected to silica gel column chromatography with a mixed solvent of benzene and ethyl acetate to give 0.6 g (90% yield) of the title compound as a pale brown viscous liquid $n_D^{21}$ 1.5510.

| NMR: | δ (ppm) | 8.0–8.2 | Aromatic | 2H |
|---|---|---|---|---|
| | δ (ppm) | 7.6–7.9 | Aromatic | 3H |
| | δ (ppm) | 4.4–4.7 | COOCH$_2$— | |
| | δ (ppm) | 1.3–1.5 | COOCH$_2$—CH$_3$ | |
| | δ (ppm) | 3.9 | —O—$\overset{\text{C}}{\underset{\text{O}}{\|}}$—OCH$_3$ | |
| | δ (ppm) | 4.1 | —O—$\overset{\text{C}}{\underset{\text{O}}{\|}}$—OCH$_3$ | |

EXAMPLE 19

3,4-Di(N,N-dimethylcarbamoyloxy)-2-carbethoxy-5-(p-methylbenzoyl)-thiophene (Compound No. 287)

To a solution of 1 g (0.0033 mol) of 3,4-dihydroxy-2-carbethoxy-5-(p-methylbenzoyl)thiophene in 30 ml of benzene are added 1 g (0.01 mol) of triethylamine and 0.9 g (0.008 mol) of N,N-dimethylcarbamoyl chloride, and the mixture is heated with stirring at 50°–70° C. for 3 hours. The reaction liquid is then washed with water, dried over anhydrous sodium sulfate, and distilled under reduced pressure to remove the solvent therefrom. The residue obtained is subjected to silica gel chromatography with a mixed solvent of benzene and ethyl acetate to give 1.2 g (82% yield) of the title compound as a reddish brown liquid, $n_D^{25}$ 1.5382.

| NMR: | δ (ppm) | 2.45 | CH₃—⟨aromatic⟩ | |
|---|---|---|---|---|
| | δ (ppm) | 7.8–7.9 | Aromatic | 2H |
| | δ (ppm) | 7.3–7.4 | Aromatic | 2H |
| | δ (ppm) | 4.3–4.5 | COOCH₂— | |
| | δ (ppm) | 1.3–1.4 | COOCH₂—CH₃ | |
| | δ (ppm) | 2.8 | —CN(=O)(CH₃)(CH₃) | |
| | δ (ppm) | 3.1–3.2 | | |

EXAMPLE 20

3,4-Di(methanesulfonyloxy)-2-carbethoxy-5-benzoyl-thiophene (Compound No. 290)

To a solution of 0.6 g (0.0020 mol) of 3,4-dihydroxy-2-carbethoxy-5-benzoylthiophene in 50 ml of benzene are added 0.8 g of triethylamine and 0.8 g (0.007 mol) of methanesulfonyl chloride, and the mixture is stirred for 2 hours while warming at 50°–70° C. to undergo reaction. The reaction liquid is then washed successively with a dilute aqueous sodium hydroxide solution and then with water. The benzene layer separated is dried over anhydrous sodium sulfate and then distilled under reduced pressure to remove the solvent therefrom. The residue obtained is subjected to silica gel chromatography with a mixed solvent of benzene and ethyl acetate to give 0.4 g (45% yield) of the title compound as a brown liquid, $n_D^{25}$ 1.5439.

| Mass spectrum (m/e) | 448 | Parent peak (P) |
|---|---|---|
| | 369 | P-79 (CH₃SO₂) |
| | 323 | P-125 (CH₃SO₂ + C₂H₅OH) |
| | 105 | Base peak (C₆H₅—C⊕=O) |
| | 77 |  |

EXAMPLE 21

3,4-Di(2'-ethoxyethylcarbonyloxy)-2,5-dicarbethoxy-thiophene (Compound No. 295)

To an ice-cold solution of 3.9 g (0.015 mol) of 3,4-dihydroxy-2,5-dicarbethoxythiophene and 5.0 g (0.037 mol) of 2-ethoxy-propionyl chloride in 50 ml of dioxane is added dropwise with stirring 15 ml of triethylamine. After completion of the addition, the mixture is heated at 60° C. for 1 hour. The reaction liquid is then poured into 150 ml of water and extracted with 200 ml of benzene. The extract is dried over anhydrous sodium sulfate and then distilled under reduced pressure to remove the solvent therefrom, whereby 4.9 g of the title compound is obtained as a yellowish brown viscous liquid, $n_D^{25.5}$ 1.4929.

Elemental analysis (for $C_{18}H_{28}O_8S$): Calculated (%): C 46.96; H 6.09. Found (%): C 46.91; H 6.07.

EXAMPLE 22

3,4-Di-(2'-furoyloxy)-2,5-dicarbethoxythiophene (Compound No. 296)

To an ice-cold solution of 2.6 g (0.01 mol) of 3,4-dihydroxy-2,5-dicarbethoxythiophene and 3.1 g (0.024 mol) of furoyl chloride in 50 ml of dioxane is added dropwise with stirring 10 ml of triethylamine. After completion of the addition, the mixture is heated at 60° C. for 1 hour. The reaction liquid is then poured into 200 ml of water, and the deposited crystals are separated by filtration. Recrystallization from ethanol gives 3.8 g (85% yield) of the title compound as white needles, m.p. 137.1° C.

Elemental analysis (for $C_{22}H_{18}O_{10}S$): Calculated (%): C 58.93; H 4.02. Found (%): C 58.85; H 4.05.

EXAMPLE 23

3,4-Di-(2'-thenoyloxy)-2,5-dicarbethoxythiophene (Compound No. 299)

To an ice-cold solution of 3.9 g (0.015 mol) of 3,4-dihydroxy-2,5-dicarbethoxy-thiophene and 5.3 g (0.036 mol) of thenoyl chloride in 50 ml of dioxane is added dropwise with stirring 15 ml of triethylamine. After completion of the addition, the mixture is stirred at 60° C. for 1 hour. The reaction liquid is then poured into 200 ml of water, and the deposited crystals are separated by filtration. Recrystallization from ethanol gives 5.3 g (74% yield) of the title compound as white columns, m.p. 132.8° C.

Elemental analysis (for $C_{22}H_{18}O_8S_3$): Calculated (%): C 55.23; H 3.77. Found (%): C 55.18; H 3.81.

Exemplified below in Tables 1a through 1e are the compounds of the present invention as prepared according to the procedures described in the foregoing examples. The compound number assigned to each compound in the tables will be referred to in examples and test examples that follow.

TABLE 1a

XO\\ /OX
  \\/
  ||
R6OOC—S—COOR6

| Compound No. | OX | COOR6 | Physicochemical data [m.p. (°C.) or refractive index $n_D$] |
|---|---|---|---|
| 1 | OCOCH$_3$ | COOCH$_3$ | m.p. 106.8 |
| 2 | " | COOC$_2$H$_5$ | m.p. 82–83 |
| 3 | " | COOC$_3$H$_7$—n | m.p. 46–48 |
| 4 | " | COOC$_3$H$_7$—i | m.p. 87.1 |
| 5 | " | COOC$_4$H$_9$—n | $n_D^{23}$ 1.4991 |
| 6 | " | COOC$_4$H$_9$—i | $n_D^{28}$ 1.4945 |
| 7 | " | COOCH$_2$CH=CH$_2$ | m.p. 67–68 |
| 8 | OCOOCH$_3$ | COOCH$_2$C≡CH | $n_D^{21}$ 1.5191 |
| 9 | OCOCH$_3$ | COOC$_6$H$_{13}$—n | $n_D^{21}$ 1.4658 |
| 10 | OCOC$_2$H$_5$ | COOC$_2$H$_5$ | $n_D^{30}$ 1.4985 |
| 11 | OCOC$_3$H$_7$—i | " | $n_D^{29}$ 1.4935 |
| 12 | OCOC$_4$H$_9$—n | COOC$_2$H$_5$ | $n_D^{26.5}$ 1.4943 |
| 13 | " | COOC$_3$H$_7$—n | $n_D^{27}$ 1.4884 |
| 14 | " | COOC$_4$H$_9$—i | $n_D^{27}$ 1.4740 |
| 15 | OCOCH=CHCH$_3$ | COOC$_2$H$_5$ | $n_D^{29}$ 1.5232 |
| 16 | OCOCH=C(CH$_3$)$_2$ | COOC$_2$H$_5$ | m.p. 74.0 |
| 17 | OCOCH$_2$Cl | " | $n_D^{30}$ 1.5174 |
| 18 | OCOCH$_2$OCH$_3$ | " | $n_D^{30}$ 1.5004 |
| 19 | OCOCH$_3$OC$_2$H$_5$ | " | $n_D^{29}$ 1.4960 |
| 20 | OCOCH$_2$SCH$_3$ | " | $n_D^{30}$ 1.5370 |
| 21 | OCOOCH$_3$ | COOCH$_3$ | m.p. 118.0 |
| 22 | " | COOC$_2$H$_5$ | m.p. 87–88 |
| 23 | " | COOC$_3$H$_7$—n | $n_D^{29}$ 1.4950 |
| 24 | " | COOC$_3$H$_7$—i | $n_D^{26}$ 1.4892 |
| 25 | " | COOC$_4$H$_9$—n | $n_D^{27.5}$ 1.4963 |
| 26 | " | COOC$_4$H$_9$—i | $n_D^{27}$ 1.4911 |
| 27 | " | COOCH$_2$CH=CH$_2$ | $n_D^{21}$ 1.5158 |
| 28 | " | COOC$_6$H$_{13}$—n | $n_D^{21}$ 1.4750 |
| 29 | OCOOC$_2$H$_5$ | COOCH$_3$ | m.p. 53.2 |
| 30 | " | COOC$_2$H$_5$ | m.p. 54.2 |
| 31 | " | COOC$_3$H$_7$—n | $n_D^{28}$ 1.4885 |
| 32 | " | COOC$_3$H$_7$—i | $n_D^{26}$ 1.4820 |
| 33 | " | COOC$_4$H$_9$—n | $n_D^{28}$ 1.4860 |
| 34 | " | COOC$_4$H$_9$—i | $n_D^{27}$ 1.4752 |
| 35 | " | COOCH$_2$CH=CH$_2$ | $n_D^{21}$ 1.5052 |
| 36 | OCOOC$_3$H$_7$—n | COOCH$_3$ | $n_D^{27.5}$ 1.4631 |
| 37 | OCOOC$_3$H$_7$—i | " | m.p. 81.8 |
| 38 | " | COOC$_3$H$_7$—i | m.p. 59.8 |
| 39 | " | COOC$_4$H$_9$—n | m.p. 69.6 |
| 40 | OCOOC$_4$H$_9$—n | COOCH$_3$ | $n_D^{27.5}$ 1.4853 |
| 41 | " | COOC$_3$H$_7$—i | m.p. 59.8 |
| 42 | OCOOCH$_2$—C$_6$H$_5$ | COOCH$_3$ | $n_D^{27.5}$ 1.5558 |
| 43 | " | COOC$_3$H$_7$—i | $n_D^{28}$ 1.5356 |
| 44 | OCOO—C$_6$H$_5$ | COOCH$_3$ | m.p. 133–134 |
| 45 | OCOSC$_2$H$_5$ | COOC$_2$H$_5$ | $n_D^{26.5}$ 1.5370 |
| 46 | OCOSC$_3$H$_7$—i | COOCH$_3$ | m.p. 96–98 |
| 47 | " | COOC$_2$H$_5$ | m.p. 47–49 |
| 48 | " | COOC$_4$H$_9$—n | $n_D^{27}$ 1.5160 |
| 49 | OCONHCH$_3$ | COOCH$_3$ | m.p. 172.4 |
| 50 | " | COOC$_2$H$_5$ | m.p. 152–153 |
| 51 | " | COOC$_3$H$_7$—n | m.p. 113.2 |
| 52 | " | COOC$_3$H$_7$—i | m.p. 146.4 |
| 53 | " | COOC$_4$H$_9$—n | m.p. 110.6 |
| 54 | " | COOC$_4$H$_9$—i | m.p. 125–127 |
| 55 | " | COOCH$_2$CH=CH$_2$ | m.p. 120–123 |
| 56 | OCONHC$_2$H$_5$ | COOCH$_3$ | m.p. 129–132 |
| 57 | " | COOC$_2$H$_5$ | m.p. 115–116 |

TABLE 1a-continued

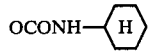

| Compound No. | OX | COOR$_6$ | Physicochemical data [m.p. (°C.) or refractive index n$_D$] |
|---|---|---|---|
| 58 | " | COOC$_3$H$_7$—n | m.p. 100–102 |
| 59 | " | COOC$_3$H$_7$—i | m.p. 100.7 |
| 60 | " | COOC$_4$H$_9$—n | m.p. 108.7 |
| 61 | " | COOC$_4$H$_9$—i | m.p. 124–125 |
| 62 | OCONHC$_3$H$_7$—n | COOCH$_3$ | m.p. 152–154 |
| 63 | " | COOC$_2$H$_5$ | m.p. 98.4 |
| 64 | " | COOC$_3$H$_7$—n | m.p. 115–116 |
| 65 | " | COOC$_3$H$_7$—i | m.p. 122.1 |
| 66 | " | COOC$_4$H$_9$—n | m.p. 87.7 |
| 67 | " | COOC$_4$H$_9$—i | m.p. 94–96 |
| 68 | OCONHC$_3$H$_7$—i | COOCH$_3$ | m.p. 149–151 |
| 69 | " | COOC$_2$H$_5$ | m.p. 125.9 |
| 70 | " | COOC$_3$H$_7$—n | m.p. 112–114 |
| 71 | " | COOC$_3$H$_7$—i | m.p. 134.6 |
| 72 | " | COOC$_4$H$_9$—n | m.p. 127.5 |
| 73 | " | COOC$_4$H$_9$—i | m.p. 127–129 |
| 74 | OCONHC$_4$H$_9$—n | COOCH$_3$ | m.p. 133–137 |
| 75 | " | COOC$_2$H$_5$ | m.p. 120–121 |
| 76 | " | COOC$_3$H$_7$—n | m.p. 105–106 |
| 77 | " | COOC$_3$H$_7$—i | m.p. 90.4 |
| 78 | " | COOC$_4$H$_9$—n | m.p. 78.7 |
| 79 | " | COOC$_4$H$_9$—i | m.p. 89–90 |
| 80 | OCON(CH$_3$)$_2$ | COOC$_2$H$_5$ | m.p. 102.6 |
| 81 | " | COOC$_3$H$_7$—n | n$_D^{26}$ 1.5150 |
| 82 | " | COOC$_4$H$_9$—n | m.p. 67–69 |
| 83 | OCONH—⟨H⟩ | COOCH$_3$ | m.p. 168–171 |
| 84 | " | COOC$_2$H$_5$ | m.p. 169.9 |
| 85 | " | COOC$_3$H$_7$—n | m.p. 163–164 |
| 86 | " | COOC$_3$H$_7$—i | m.p. 149.8 |
| 87 | " | COOC$_4$H$_9$—i | m.p. 166–167 |
| 88 | OSO$_2$CH$_3$ | COOCH$_3$ | m.p. 131–132 |
| 89 | " | COOC$_2$H$_5$ | n$_D^{28}$ 1.5228 |
| 90 | " | COOC$_3$H$_7$—n | n$_D^{30}$ 1.5132 |
| 91 | " | COOC$_3$H$_7$—i | n$_D^{27}$ 1.510 |
| 92 | " | COOC$_4$H$_9$—n | n$_D^{28}$ 1.5100 |
| 93 | " | COOC$_4$H$_9$—i | n$_D^{28}$ 1.5083 |
| 94 | OSO$_2$C$_2$H$_5$ | COOC$_2$H$_5$ | n$_D^{30}$ 1.5163 |
| 95 | OSO$_2$—⟨⟩—CH$_3$ | COOCH$_3$ | m.p. 158–160 |
| 96 | " | COOC$_2$H$_5$ | m.p. 125–127 |
| 97 | " | COOC$_3$H$_7$—n | m.p. 83–86 |
| 98 | " | COOC$_3$H$_7$—i | m.p. 116–117 |
| 99 | " | COOC$_4$H$_9$—n | n$_D^{28}$ 1.5435 |
| 100 | " | COOC$_4$H$_9$—i | n$_D^{26}$ 1.5467 |
| 101 | " | COOCH$_2$—CH=CH$_2$ | m.p. 65–66 |
| 102 | " | COOCH$_2$C≡CH | n$_D^{21}$ 1.5759 |
| 103 | OSO$_2$N(CH$_3$)$_2$ | COOC$_3$H$_7$—n | n$_D^{30}$ 1.4980 |
| 104 | OSO$_2$N(C$_2$H$_5$)$_2$ | COOC$_2$H$_5$ | n$_D^{30}$ 1.5080 |
| 105 | OCO—⟨⟩ | " | m.p. 96.2 |
| 106 | " | COOC$_3$H$_7$—n | n$_D^{29}$ 1.5600 |
| 107 | " | COOC$_4$H$_9$—i | n$_D^{28}$ 1.5500 |
| 108 | OP(S)(OC$_2$H$_5$)$_2$ | COOC$_2$H$_5$ | m.p. 105.6 |
| 109 | OP(S)(OCH$_3$)$_2$ | COOCH$_3$ | m.p. 89.9 |
| 110 | OCON(CH$_3$)$_2$ | COOC$_4$H$_9$—i | m.p. 94–95 |
| 111 | OP(S)(OCH$_3$)$_2$ | COOC$_2$H$_5$ | m.p. 77.6 |
| 112 | " | COOC$_3$H$_7$—n | m.p. 52.2 |
| 113 | OCOCH$_2$Cl | " | n$_D^{22}$ 1.5210 |
| 114 | OCOC$_2$H$_5$ | " | n$_D^{22}$ 1.4980 |
| 115 | OCOCH$_2$OCH$_3$ | " | n$_D^{22}$ 1.5017 |
| 116 | OCOCH$_2$SCH$_3$ | " | n$_D^{20}$ 1.5389 |

TABLE 1a-continued

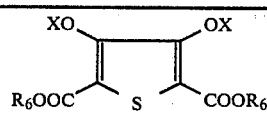

| Compound No. | OX | COOR$_6$ | Physicochemical data [m.p. (°C.) or refractive index $n_D$] |
|---|---|---|---|
| 117 | OCOC$_3$H$_7$—n | " | $n_D^{21}$ 1.4912 |
| 118 | OCOCH$_2$OC$_2$H$_5$ | " | $n_D^{20}$ 1.4972 |
| 119 | OCONHC$_2$H$_5$ | COOCH$_2$CH=CH$_2$ | m.p. 113–114 |
| 120 | OCONHC$_3$H$_7$—n | " | m.p. 103–104 |
| 121 | OCOC$_3$H$_7$—n | COOC$_4$H$_9$—n | $n_D^{11}$ 1.4887 |
| 122 | OCOC$_2$H$_5$ | " | $n_D^{11}$ 1.4991 |
| 123 | OCOCH$_2$Cl | " | $n_D^{11}$ 1.5168 |
| 124 | OCOCH$_2$OCH$_3$ | " | $n_D^{11}$ 1.4992 |
| 125 | OCOCH$_2$OC$_2$H$_5$ | " | $n_D^{11}$ 1.4921 |
| 126 | OCOCH$_2$SCH$_3$ | " | $n_D^{11}$ 1.5340 |
| 127 | OCOC$_3$H$_7$—n | COOC$_2$H$_5$ | $n_D^{17}$ 1.4974 |
| 128 | OCOCH$_2$Cl | COOCH$_2$CH=CH$_2$ | $n_D^{19}$ 1.5392 |
| 129 | OCOC$_2$H$_5$ | " | $n_D^{17}$ 1.5160 |
| 130 | OCOC$_3$H$_7$—n | " | $n_D^{16}$ 1.5073 |
| 131 | OCOCH$_2$OCH$_3$ | " | $n_D^{19}$ 1.5231 |
| 132 | OCOCH$_2$OC$_2$H$_5$ | " | $n_D^{20}$ 1.5080 |
| 133 | OCOCH$_2$SCH$_3$ | " | $n_D^{19}$ 1.5542 |
| 134 | OCOCH$_2$OCH$_3$ | COOCH$_2$C≡CH | m.p. 86–87 |
| 135 | OCOCH$_2$SCH$_3$ | " | m.p. 88–89 |
| 136 | OCOCH$_2$OC$_2$H$_5$ | " | m.p. 71–72 |
| 137 | OCOC$_2$H$_5$ | COOC$_3$H$_7$—i | m.p. 62.6 |
| 138 | OCOC$_3$H$_7$—n | " | $n_D^{10.5}$ 1.4858 |
| 139 | OCOCH$_2$OCH$_3$ | " | $n_D^{10}$ 1.500 |
| 140 | OCOCH$_2$OC$_2$H$_5$ | " | $n_D^{10}$ 1.4945 |
| 141 | OCOCH$_2$SCH$_3$ | " | $n_D^{10}$ 1.5378 |
| 142 | OCOCH$_2$Cl | " | $n_D^{10}$ 1.5177 |
| 143 | OCOCH$_2$OC$_2$H$_5$ | COOCH$_3$ | m.p. 120.4 |
| 144 | OCOCH=CH$_2$ | " | $n_D^{22.5}$ 1.5269 |
| 145 | " | COOC$_3$H$_7$—n | $n_D^{27}$ 1.5165 |
| 146 | OCOCH$_2$Cl | COOCH$_3$ | m.p. 95.0 |
| 147 | OCOCH$_2$OCH$_3$ | " | m.p. 99.6 |
| 148 | OCOCH=CH$_2$ | " | m.p. 83.0 |
| 149 | OCOC$_2$H$_5$ | " | m.p. 64.5 |
| 150 | OCOC$_4$H$_9$—t | " | m.p. 127.9 |
| 151 | OCOC$_3$H$_7$—n | " | m.p. 45.1 |
| 152 | OCOCH=CH—CH$_3$ | " | m.p. 131.6 |
| 153 | OCOC$_3$H$_7$—i | COOCH$_3$ | m.p. 66.7 |
| 154 | OCOCH$_3$ | COOCH$_2$C≡CH | m.p. 113.5 |
| 155 | OCOCH=CH$_2$ | COOCH$_2$CH=CH$_2$ | $n_D^{23}$ 1.5337 |
| 156 | " | COOCH$_2$C≡CH | m.p. 88.1 |
| 157 | OCOC$_2$H$_5$ | " | m.p. 106.2 |
| 158 | OCOCH$_2$SCH$_3$ | COOCH$_3$ | m.p. 79–80 |

TABLE 1b

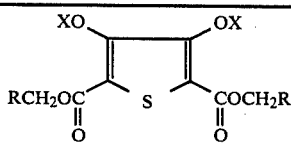

| Compound No. | X | CH$_2$R | Physicochemical data [m.p. (°C.) or refractive index $n_D$] |
|---|---|---|---|
| 159 | H | CH$_2$CH$_2$OC$_2$H$_5$ | m.p. 79–80 |
| 160 | COOCH$_3$ | " | $n_D^{19}$ 1.5040 |
| 161 | CONHCH$_3$ | " | m.p. 87.5 |
| 162 | COCH$_3$ | " | $n_D^{19}$ 1.5021 |
| 163 | COCH$_2$Cl | " | $n_D^{27}$ 1.5123 |
| 164 | COCH$_2$OCH$_3$ | " | $n_D^{27}$ 1.4902 |
| 165 | COCH$_2$SCH$_3$ | " | $n_D^{27}$ 1.5288 |
| 166 | COC$_2$H$_5$ | " | $n_D^{27}$ 1.4890 |
| 167 | COCH—CH$_3$<br>\|<br>Cl | " | $n_D^{27}$ 1.4976 |
| 168 | H | CH$_2$CH$_2$OCH$_3$ | m.p. 126.5 |
| 169 | COCH$_3$ | " | m.p. 67.7 |
| 170 | COCH$_2$OCH$_3$ | " | m.p. 81.2 |
| 171 | COCH$_2$Cl | " | m.p. 83.8 |
| 172 | COCH$_2$SCH$_3$ | " | $n_D^{27}$ 1.5060 |
| 173 | COCHCH$_3$<br>\|<br>Cl | " | $n_D^{27}$ 1.5190 |
| 174 | COCH=CH$_2$ | " | $n_D^{27}$ 1.5190 |

TABLE 1b-continued

Structure: XO and OX on a thiophene ring with RCH₂CO- and -COCH₂R substituents

| Compound No. | X | CH₂R | Physicochemical data [m.p. (°C.) or refractive index $n_D$] |
|---|---|---|---|
| 175 | COC₂H₅ | " | $n_D^{27}$ 1.4897 |
| 176 | COOCH₃ | " | m.p. 92.1 |
| 177 | H | CH₂–(phenyl) | m.p. 153–154 |
| 178 | COCH₃ | " | m.p. 95.7 |
| 179 | COOCH₃ | " | m.p. 103.4 |
| 180 | COCH₂Cl | " | m.p. 102.9 |
| 181 | CO–(furyl) | " | Rf((phenyl)) 0.3 |
| 182 | COCH₂OCCH₃ (with C=O) | " | $n_D^{27}$ 1.5366 |
| 183 | CONHC₂H₅ | " | m.p. 158–159 |
| 184 | CONH–(cyclohexyl H) | " | m.p. 145–148 |
| 185 | CON(C₂H₅)₂ | " | $n_D^{27}$ 1.5145 |
| 186 | CO–(2,4-dichlorophenyl) | CH₂CH₂OC₂H₅ | $n_D^{25}$ 1.5781 |
| 187 | CO–(cyclopropyl) | " | $n_D^{25}$ 1.5088 |
| 188 | CO–(thienyl) | " | m.p. 80–81 |
| 189 | COO–(phenyl) | " | $n_D^{31}$ 1.5333 |
| 190 | COCH₂OCCH₃ (with C=O) | " | $n_D^{30}$ 1.4803 |
| 191 | COSC₃H₇—i | " | $n_D^{30}$ 1.5126 |
| 192 | COOCH₂–(phenyl) | " | $n_D^{25}$ 1.5399 |
| 193 | SO₂–(phenyl)–CH₃ | " | m.p. 67–68 |
| 194 | SO₂CH₃ | " | $n_D^{21}$ 1.5159 |
| 195 | SO₂N(CH₃)₂ | " | $n_D^{21}$ 1.5012 |
| 196 | CONH–(cyclohexyl H) | " | m.p. 129–130 |
| 197 | CON–(piperidinyl) | CH₂–(phenyl) | $n_D^{24}$ 1.5770 |
| 198 | COO–(phenyl) | " | $n_D^{24}$ 1.5843 |
| 199 | SO₂C₂H₅ | " | $n_D^{24}$ 1.5585 |
| 200 | SO₂N(CH₃)₂ | " | $n_D^{22}$ 1.5664 |
| 201 | SO₂–(phenyl)–CH₃ | " | $n_D^{21}$ 1.5954 |
| 202 | COSC₄H₉—n | " | $n_D^{24}$ 1.5624 |
| 203 | COOCH₂–(phenyl) | " | $n_D^{24}$ 1.5811 |
| 204 | P(OCH₃)₂ with S= | " | $n_D^{20}$ 1.5448 |

TABLE 1c

| Compound No. | X | R₆ | Physicochemical data [m.p. (°C.) or refractive index $n_D$] |
|---|---|---|---|
| 205 | COCH₃ | CH₃ | m.p. 112–113 |
| 206 | H | " | m.p. 250 |
| 207 | CONHCH₃ | " | m.p. 159–160 |
| 208 | CONHC₂H₅ | " | m.p. 118–121 |
| 209 | CONHC₄H₉—n | " | m.p. 116–118 |
| 210 | H | C₂H₅ | 117–180 (dec.) |
| 211 | Na | " | m.p. >280 |
| 212 | COCH₃ | " | m.p. 92–94 |
| 213 | CONHCH₃ | " | 144–146 (dec.) |
| 214 | CONHC₂H₅ | " | m.p. 92–94 |
| 215 | CON(CH₃)₂ | " | $n_D^{27}$ 1.5300 |
| 216 | COOC₂H₅ | " | m.p. 53–54 |
| 217 | COOCH₃ | " | m.p. 70.4 |
| 218 | CONHC₃H₇—n | " | m.p. 121–122 |
| 219 | CONHC₃H₇—i | " | m.p. 137–140 |
| 220 | CONHC₄H₉—n | " | m.p. 106–107 |
| 221 | CONH–(cyclohexyl H) | " | m.p. 131–133 |
| 222 | COOCH₃ | CH₃ | m.p. 78.5 |
| 223 | COOC₂H₅ | " | m.p. 64.2 |
| 224 | COOC₃H₇—n | " | $n_D^{12.5}$ 1.4981 |
| 225 | COC₂H₅ | C₂H₅ | $n_D^{10.5}$ 1.5105 |
| 226 | COC₃H₇—n | " | $n_D^{10.5}$ 1.5075 |
| 227 | COCH₂OCH₃ | " | $n_D^{10}$ 1.5220 |
| 228 | COCH₂OC₂H₅ | " | $n_D^{10}$ 1.5119 |

TABLE 1c-continued

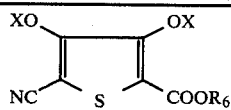

| Compound No. | X | R6 | Physicochemical data [m.p. (°C.) or refractive index $n_D$] |
|---|---|---|---|
| 229 | COCH2SCH3 | " | m.p. 70.4 |
| 230 | COCH2Cl | " | $n_D^{21}$ 1.5453 |
| 231 | COCH3 | C3H7—n | m.p. 52.8 |
| 232 | COOC2H5 | " | $n_D^{21.5}$ 1.4990 |
| 233 | COOC3H7—n | " | $n_D^{21.5}$ 1.4913 |
| 234 | CO—△ | C2H5 | $n_D^{25}$ 1.5295 |
| 235 | CO—(furan) | " | m.p. 127–128 |
| 236 | COCH2OCCH3 (O) | " | $n_D^{25}$ 1.5060 |
| 237 | CO—N(pyrrolidine) | " | $n_D^{27}$ 1.5458 |

TABLE 1c-continued

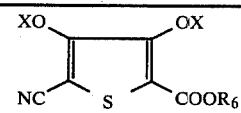

| Compound No. | X | R6 | Physicochemical data [m.p. (°C.) or refractive index $n_D$] |
|---|---|---|---|
| 238 | COO—⌬ | " | m.p. 98–101 |
| 239 | COOCH2—⌬ | " | $n_D^{27}$ 1.5495 |
| 240 | COSC3H7—n | " | $n_D^{26}$ 1.5386 |
| 241 | SO2C2H5 | " | m.p. 102–103 |
| 242 | SO2—⌬—CH3 | " | m.p. 117–120 |
| 243 | SO2N(CH3)2 | " | m.p. 93–95 |
| 244 | CO—(H) | " | $n_D^{25}$ 1.5630 |
| 245 | S‖P(OCH3)2 | " | m.p. 81.4 |

TABLE 1d

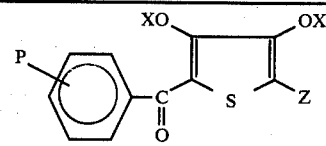

| Compound No. | X | P (phenyl substituent) | Z | Physicochemical data [m.p. (°C.) or refractive index $n_D$] |
|---|---|---|---|---|
| 246 | H | ⌬ | COOCH3 | m.p. 136–138 |
| 247 | " | " | COOC2H5 | m.p. 147–148 |
| 248 | " | Cl—⌬— | " | m.p. 140–142 |
| 249 | COCH3 | ⌬ | " | $n_D^{22}$ 1.5710 |
| 250 | H | " | H | m.p. 152–154 (dec.) |
| 251 | OCOCH3 | " | " | $n_D^{23}$ 1.5380 |
| 252 | " | " | COOC2H5 | $n_D^{21}$ 1.5510 |
| 253 | OCOC2H5 | " | " | $n_D^{20}$ 1.5195 |
| 254 | COCH2OCH3 | " | " | $n_D^{20}$ 1.5392 |
| 255 | OCOC2H5 | " | H | $n_D^{18}$ 1.5132 |
| 256 | COCH3 | " | COOCH3 | $n_D^{27}$ 1.5595 |
| 257 | COC2H5 | " | " | $n_D^{27}$ 1.5430 |
| 258 | OCOCH3 | " | " | Rf(φH) 0.3 |

TABLE 1d-continued

[Structure: P-phenyl-C(=O)- attached to thiophene ring with XO and OX substituents at positions 3,4 and Z at position 5]

| Compound No. | X | P (phenyl) | Z | Physicochemical data [m.p. (°C.) or refractive index $n_D$] |
|---|---|---|---|---|
| 259 | OCOC$_2$H$_5$ | " | " | $n_D^{25}$ 1.5483 |
| 260 | COC$_2$H$_5$ | " | COOC$_2$H$_5$ | $n_D^{26}$ 1.5513 |
| 261 | SCOC$_3$H$_7$—n | " | " | $n_D^{28}$ 1.5694 |
| 262 | COCH$_2$OC$_2$H$_5$ | " | " | $n_D^{28}$ 1.5328 |
| 263 | H | " | COOC$_3$H$_7$—i | m.p. 130–132 |
| 264 | OCOCH$_3$ | " | " | Rf($\phi$) 0.37 |
| 265 | H | " | CO— [phenyl] | m.p. 179–181 |
| 266 | OCOC$_2$H$_5$ | " | " | $n_D^{26}$ 1.5681 |
| 267 | COCH$_2$OCH$_3$ | " | COOCH$_3$ | $n_D^{26}$ 1.5670 |
| 268 | COCH=CHCH$_3$ | " | " | $n_D^{28}$ 1.5930 |
| 269 | CO—[cyclopropyl] | " | " | $n_D^{27}$ 1.5608 |
| 270 | COCH$_2$SCH$_3$ | " | " | $n_D^{27}$ 1.6020 |
| 271 | COCH$_2$OC$_2$H$_5$ | " | " | $n_D^{27}$ 1.5533 |
| 272 | COSC$_3$H$_7$—n | " | " | $n_D^{25}$ 1.5772 |
| 273 | CO—[cyclopropyl] | " | COOC$_2$H$_5$ | $n_D^{25}$ 1.5645 |
| 274 | COCH=CH$_2$ | " | " | $n_D^{25}$ 1.5905 |
| 275 | COCH$_2$SCH$_3$ | " | " | $n_D^{27}$ 1.5913 |
| 276 | COCH$_3$ | " | COOC$_3$H$_7$—i | $n_D^{26}$ 1.5538 |
| 277 | COC$_2$H$_5$ | " | CO—[phenyl] | m.p. 179–180 |
| 278 | OCOCH$_3$ | " | " | $n_D^{27}$ 1.5762 |
| 279 | OCOC$_2$H$_5$ | Cl—[phenyl]— | COOC$_2$H$_5$ | $n_D^{25}$ 1.4991 |
| 280 | COCH$_2$OCH$_3$ | " | " | $n_D^{28}$ 1.5508 |
| 281 | COCH=CH$_2$ | " | " | $n_D^{26}$ 1.5822 |
| 282 | OCOCH$_3$ | " | " | $n_D^{29}$ 1.5578 |
| 283 | COCH$_3$ | " | " | $n_D^{29}$ 1.5605 |
| 284 | H | CH$_3$—[phenyl]— | " | m.p. 139–141 |
| 285 | OCOC$_2$H$_5$ | " | " | $n_D^{26}$ 1.5358 |
| 286 | OCOCH$_3$ | " | " | $n_D^{26}$ 1.5470 |
| 287 | CON(CH$_3$)$_2$ | " | " | $n_D^{25}$ 1.5382 |
| 288 | COCH$_3$ | " | " | m.p. 79–81 |
| 289 | COCH=CH$_2$ | " | " | $n_D^{26}$ 1.5748 |
| 290 | SO$_2$CH$_3$ | [phenyl]— | " | $n_D^{25}$ 1.5439 |

TABLE 1e

Structure:
- Thiophene ring with OX groups at positions 3 and 4
- COOR6 groups at positions 2 and 5

| Compound No. | X | R6 | Physicochemical data [m.p. (°C.) or refractive index $n_D$] |
|---|---|---|---|
| 291 | CO-(2-pyridyl) | $C_2H_5$ | m.p. 96.4 |
| 292 | CO-(2-furyl) | $CH_3$ | m.p. 161.2 |
| 293 | CO-(2-thienyl) | " | m.p. 191.4 |
| 294 | CO—CH(CH$_3$)—Cl | $C_2H_5$ | $n_D^{25.5}$ 1.5150 |
| 295 | CO—CH$_2$CH$_2$OC$_2$H$_5$ | " | $n_D^{25.5}$ 1.4929 |
| 296 | CO-(2-furyl) | " | m.p. 137.1 |
| 297 | CO-cyclopropyl | " | $n_D^{25.5}$ 1.5221 |
| 298 | COCH(CH$_3$)OCOCH$_3$ | " | $n_D^{25.5}$ 1.4916 |
| 299 | CO-(2-thienyl) | " | m.p. 132.8 |
| 300 | COCH$_2$OCOCH$_3$ | " | $n_D^{25.5}$ 1.5042 |
| 301 | COCH(CH$_3$)Cl | $C_3H_7$—n | $n_D^{27}$ 1.5050 |
| 302 | CO—CH(CH$_3$)—Cl | $CH_3$ | $n_D^{26}$ 1.5204 |
| 303 | CO-cyclopropyl | " | m.p. 91 |
| 304 | COCH$_2$CH$_2$OC$_2$H$_5$ | " | $n_D^{27}$ 1.4970 |
| 305 | CO—CH(CH$_3$)—Br | $C_2H_5$ | $n_D^{27}$ 1.5270 |
| 306 | " | $C_3H_7$—n | $n_D^{27}$ 1.5168 |
| 307 | CO—CH$_2$Br | $C_2H_5$ | $n_D^{27}$ 1.5392 |
| 308 | " | $C_3H_7$—n | $n_D^{27}$ 1.5333 |
| 309 | CO—CH(CH$_3$)—Cl | —CH$_2$—CH=CH$_2$ | $n_D^{27}$ 1.5260 |

TABLE 1e-continued

Structure: X-C(=O)- and -C(=O)-X on thiophene ring with R₆OOC- and -COOR₆ substituents (thiophene with S)

| Compound No. | X | $R_6$ | Physicochemical data [m.p. (°C.) or refractive index $n_D$] |
|---|---|---|---|
| 310 | CO—CH(CH₃)—Br | " | $n_D^{27}$ 1.5340 |
| 311 | COCH₂CH₂C(=O)CH₃ | $C_2H_5$ | $n_D^{28}$ 1.4958 |
| 312 | COOCH₂CH₂Br | " | $n_D^{25}$ 1.5252 |
| 313 | COOCH₂CH₂OCH₃ | " | $n_D^{25}$ 1.4949 |
| 314 | " | $CH_3$ | $n_D^{25}$ 1.5006 |
| 315 | COOCH₂C(=O)C₂H₅ | $C_2H_5$ | $n_D^{25}$ 1.4909 |
| 316 | COOCH₂CH=CH₂ | " | $n_D^{31}$ 1.5031 |
| 317 | COOCH₂C≡CH | " | $n_D^{30}$ 1.5058 |
| 318 | COCH₂OC(=O)CH₃ | $CH_2CH=CH_2$ | $n_D^{30}$ 1.4990 |
| 319 | COOCH₂CH₂Cl | $CH_3$ | m.p. 94–100 |
| 320 | COCH₂OC(=O)CH₃ | " | m.p. 90 |
| 321 | CO—(2-thienyl) | $CH_2C\equiv CH$ | m.p. 133–134 |
| 322 | COCH₂OC(=O)CH₃ | " | $n_D^{30}$ 1.5012 |
| 323 | COOCH₂CH₂F | $CH_3$ | m.p. 75–85 |
| 324 | CO—N(pyrrolidinyl) | $CH_2CH=CH_2$ | m.p. 124–125 |
| 325 | CO—(cyclohexyl) | $CH_2C\equiv CH$ | m.p. 86–87 |
| 326 | COCH₂OCH₃ | $C_5H_{11}$—n | $n_D^{28}$ 1.4859 |
| 327 | CO—N(pyrrolidinyl) | $C_2H_5$ | m.p. 131.0 |
| 328 | CO—N(piperidinyl) | " | m.p. 106.0 |
| 329 | COCH₃ | $C_5H_{11}$—n | $n_D^{26}$ 1.4892 |

TABLE 1e-continued $$\underset{R_6OOC}{\overset{X}{\underset{\|}{O}}}\diagdown_S\diagup\underset{COOR_6}{\overset{X}{\underset{\|}{O}}}$$

| Compound No. | X | $R_6$ | Physicochemical data [m.p. (°C.) or refractive index $n_D$] |
|---|---|---|---|
| 330 | COO—⟨phenyl⟩ | " | $n_D^{25}$ 1.5277 |
| 331 | $SO_2$—⟨phenyl⟩—$CH_3$ | " | $n_D^{28}$ 1.5410 |
| 332 | CO—N⟨pyrrolidine⟩ | $CH_2C{\equiv}CH$ | m.p. 176–177 |
| 333 | $COCH_2CH_2OC_2H_5$ | $C_5H_{11}$—n | $n_D^{25}$ 1.4885 |
| 334 | $COCH_2SCH_3$ | " | $n_D^{19}$ 1.5377 |
| 335 | $SO_2CH_3$ | " | $n_D^{20}$ 1.5072 |
| 336 | $COCH_2OCOCH_3$ | " | $n_D^{25}$ 1.4822 |
| 337 | CO—⟨cyclohexyl H⟩ | " | $n_D^{23}$ 1.5056 |
| 338 | $\overset{S}{\underset{\|}{P}}(OCH_3)_2$ | " | $n_D^{24}$ 1.5160 |
| 339 | $CON(CH_3)_2$ | " | $n_D^{22}$ 1.5082 |
| 340 | CON⟨hexamethyleneimine⟩ | " | $n_D^{22}$ 1.5149 |
| 341 | $COSC_3H_7$—n | " | $n_D^{21}$ 1.5179 |
| 342 | $SO_2N(CH_3)_2$ | " | $n_D^{20}$ 1.5123 |
| 343 | $COCH_2O\overset{O}{\underset{\|}{C}}CH_3$ | $C_6H_{13}$—n | $n_D^{29}$ 1.4870 |

The compounds of the present invention can be formulated, when they are intended to be used as agricultural and horticultural fungicides, into any forms conventionally adopted in the art for these purposes, for example, such compositions as dust, wettable powder, emulsion, granule, microgranule and the like. The carrier material, used for the uniform distribution of the present compounds in effective amounts, may be either a liquid or particulate solid material, and is not limited to specific materials. Suitably usable solid carrier materials include, for example, various kinds of kaolin, clay, diatomaceous earth, talc, silica and the like. Suitably usable liquid carrier materials may be those which are inert solvents for the present active ingredient compounds and those which are non-solvents therefor but capable of dispersing or dissolving said active ingredient compounds by the aid of appropriate adjuvants used in combination therewith. Such liquid carrier materials include, for example, benzene, xylene, toluene, kerosene, alcohols, ketones, dimethyl sulfoxide, dimethylformamide and the like. By using such liquid carriers in admixture with appropriate surface active agents and other formulation aids, for example, spreading agents, sticking agents and the like, the present active ingredient compounds can be formulated into, and used as, aqueous solution or emulsions.

Furthermore, the compounds of the present invention can be used in admixture with other fungicides, insecticides, herbicides, plant growth regulators, etc. for the purpose of lessening the labor and of ensuring the controlling effect of the present compounds.

When operating in accordance with the present invention, effective amounts of the compounds or compositions of this invention are applied to the plants in any convenient fashion. The application of liquid and particulate solid compositions to plants can be carried out by conventional methods, e.g., power dusters, boom and hand sprayers and spray dusters. The compositions can also be applied from airplanes as a dust or a spray because of their effectiveness at low dosages.

The application of an effective amount of the compounds or compositions of this invention to the plant is essential for the practice of the present invention. The exact amount of active ingredient to be employed may vary depending on several factors including the response desired as well as the plant species to be treated and stage of development thereof, and the amount of rainfall as well as the specific type of compound used. Generally, however, the active ingredients are applied in amounts of from about 100 grams to about 1,000 grams per hectare.

Some examples are given below to illustrate the use as agricultural and horticultural fungicides of the compounds of the present invention in compositions of varied types, but it should be construed that both the active ingredient compounds of the present invention and additives usable in such compositions are not limited to those exemplified in these examples.

EXAMPLE 24

(Dust)

A homogeneous mixture of 2 parts of compound No. 7 and 98 parts of clay is pulverized to obtain a dust preparation containing 2% of the active ingredient.

EXAMPLE 25

(Wettable Powder)

A homogeneous mixture of 30 parts of compound No. 11, 3 parts of calcium alkylbenzenesulfonate, 5 parts of polyoxyethylenenonylphenyl ether and 62 parts of clay is pulverized to obtain a wettable powder having uniformly and finely dispersed therein all the constituents including 30% of the finely divided active ingredient. This wettable powder, when it is actually applied to plants, is diluted to 600 to 1000 times with water and then sprayed over the plants.

EXAMPLE 26

(Emulsion)

By mixing 30 parts of compound No. 12 with, and dissolving in, 55 parts of methyl ethyl ketone and 15 parts of polyoxyethylenenonylphenyl ether, an emulsion containing 30% of the active ingredient is obtained. The emulsion, when it is actually applied to plants, is diluted to 600 to 1000 time with water and then sprayed over the plants.

EXAMPLE 27

(Granule)

A mixture of 5 parts of compound No. 15, 1.5 parts of lauryl sulfate, 1.5 parts of calcium lignin sulfate, 25 parts of bentonite, 67 parts of acid clay and 15 parts of water is kneaded with a kneading machine, followed granulation. The granules thus obtained are then dried with a fluidized drier to obtain a granule preparation containing 5% of the active ingredient.

EXAMPLE 28

(Dust)

A homogeneous mixture of 2 parts of compound No. 162 and 98 parts of clay is uniformly pulverized to obtain a dust preparation containing 2% of the active ingredient.

EXAMPLE 29

(Wettable Powder)

A homogeneous mixture of 30 parts of compound No. 163, 3 parts of calcium alkylbenzenesulfonate, 5 parts of polyoxyethylenenonylphenyl ether and 62 parts of clay is pulverized to obtain a wettable powder having uniformly and finely dispersed therein all the constituents including 30% of the active ingredient. The wettable powder thus obtained, when it is actually used, is diluted 600 to 1000 times with water and then sprayed over plants.

EXAMPLE 30

(Emulsion)

By mixing 30 parts of compound No. 165 with, and dissolved in, 55 parts of methyl ethyl ketone and 15 parts of polyoxyethylenenonylphenyl ether, an emulsion containing 30% of the active ingredient is obtained. The emulsion thus obtained, when it is actually applied to plants, is diluted to 600 to 1000 times with water and then sprayed over the plants.

EXAMPLE 31

(Granule)

A mixture of 5 parts of compound No. 173, 1.5 parts of lauryl sulfate, 1.5 parts of calcium lignin sulfonate, 25 parts of bentonite, 67 parts of acid clay and 15 parts of water is kneaded with a kneading machine, followed by granulation. The granules thus obtained are then dried with a fluidized drier to obtain a granule preparation containing 5% of the active ingredient.

EXAMPLE 32

(Dust)

A homogeneous mixture of 2 parts of compound No. 220 and 98 parts of clay is uniformly pulverized to obtain a dust preparation containing 2% of the active ingredient.

EXAMPLE 33

(Wettable Powder)

A homogeneous mixture of 30 parts of compound No. 223, 3 parts of calcium alkylbenzenesulfonate, 5 parts of polyoxyethylenenonylphenyl ether and 62 parts of clay is uniformly poulverized to obtain a wettable powder having uniformly and finely dispersed therein all the constituents including 30% of the active ingredient. The thus obtained wettable powder, when it is actually applied to plants, is diluted to 600 to 1000 times with water and then sprayed over the plants.

EXAMPLE 34

(Emulsion)

By mixing 30 parts of compound No. 225 with, and dissolved in, 55 parts of methyl ethyl ketone and 15 parts of polyoxyethylenenonylphenyl ether, an emulsion containing 30% of the active ingredient is obtained.

The emulsion thus obtained, when it is actually applied to plants, is diluted to 600 to 1000 times with water and then sprayed over the plants.

EXAMPLE 35

(Granule)

A mixture of 5 parts of compound No. 232, 1.5 parts of lauryl sulfate, 1.5 parts of calcium lignin sulfonate, 25 parts of bentonite, 67 parts of acid clay and 15 parts of water is kneaded with a kneading machine, followed by granulation. The granules thus obtained are dried with a fluidized drier to obtain a granule preparation containing 5% of the active ingredient.

EXAMPLE 36

(Dust)

A homogeneous mixture of 2 parts of compound No. 252 and 98 parts of clay is uniformly pulverized to obtain a dust preparation containing 2% of the active ingredient.

EXAMPLE 37

(Wettable Powder)

A homogeneous mixture of 30 parts of compound No. 253, 3 parts of calcium alkylbenzenesulfonate, 5 parts of polyoxyethylenenonylphenyl ether and 62 parts of clay is uniformly pulverized to obtain a wettable powder having uniformly dispersed therein all the constituents including 30% of the finely divided active ingredient. The wettable powder thus obtained, when it is actually applied to plants, is diluted to 600 to 1000 times with water and then sprayed over the plants.

EXAMPLE 38

(Emulsion)

By mixing 30 parts of compound No. 256 with, and dissolving in, 55 parts of methyl ethyl ketone and 15 parts of polyoxyethylenenonylphenyl ether, an emulsion containing 30% of the active ingredient. The emulsion thus obtained, when it is actually applied to plants, is diluted to 600 to 1000 times with water and then sprayed over the plants.

EXAMPLE 39

(Granule)

A mixture of 5 parts of compound No. 258, 1.5 parts of lauryl sulfate, 1.5 parts of calcium lignin sulfonate, 25 parts of bentonite, 67 parts of acid clay and 15 parts of water is kneaded with a kneading machine, followed by granulation. The granules thus obtained are dried with a fluidized drier to obtain a granule preparation containing 5% of the active ingredient.

EXAMPLE 40

(Dust)

A homogeneous mixture of 2 parts of compound No. 297 and 98 parts of clay is uniformly pulverized to obtain a dust preparation containing 2% of the active ingredient.

Example 41

(Wettable Powder)

A homogeneous mixture of 30 parts of compound No. 301, 3 parts of calcium alkylbenzenesulfonate, 5 parts of polyoxyethylenenonylphenyl ether and 62 parts of clay is uniformly pulverized to obtain a wettable powder having uniformly and finely dispersed therein all the constituents including 30% of the active ingredient. The wettable powder thus obtained, when it is actually applied to plants, is diluted to 600 to 1000 times with water and then sprayed over the plants.

EXAMPLE 42

(Emulsion)

By mixing 30 parts of compound No. 302 with, and dissolving in, 55 parts of methyl ethyl ketone and 15 parts of polyoxyethylenenonylphenyl ether, an emulsion containing 30% of the active ingredient is obtained. The emulsion thus obtained, when it is actually applied to plants, is diluted to 600 to 1000 times with water and sprayed over the plants.

EXAMPLE 43

(Granule)

A mixture of 5 parts of compound No. 305, 1.5 parts of lauryl sulfate, 1.5 parts of calcium lignin sulfonate, 67 parts of acid clay, 25 parts of bentonit and 15 parts of water is kneaded with a kneading machine, followed by granulation. The granules thus obtained are dried with a fluidized drier to obtain a granule preparation containing 5% of the active ingredient.

Control effects on various plant diseases of the compounds of the present invention, when they are used as agricultural and horticultural fungicides, are illustrated below with reference to test examples.

TEST EXAMPLE 1

Test for Control Effect on Paddy Rice Blast

Over the 3rd-leaf stage seedlings of paddy rice (variety: Asahi) soil cultured in a biscuit pot of 9 cm in diameter in a greenhouse was sprayed a test liquid prepared by diluting a wettable powder prepared according to the general procedure of Example 25 to a predetermined concentration with water. One day after the spraying of the test liquid, the seedings were inoculated by atomizing technique with a spore suspension of rice blast fungus (*Pyricularia oryzae*). Upon completion of the inoculation, the seedlings were kept overnight under humidified circumstances (at 95-100% relative humidity and 24°-25° C.). Five (5) days after the inoculation, the number of lesions per leaf of the third stage leaves was investigated and the preventive value was calculated on the basis of the following equation. Furthermore, the phytotoxic activity against the rice plant of the test compound was investigated according to a fixed numerical scale, the injury ratings of which are defined as mentioned below. The results obtained are as shown in Table 2.

$$\text{Control value (\%)} = \left(1 - \frac{\text{Number of lesions in treated plot}}{\text{Number of lesions in blank plot}}\right) \times 100$$

| Injury rating: | |
|---|---|
| 5: | Very severe phototoxicity |
| 4: | Severe phototoxicity |
| 3: | Great phototoxicity |
| 2: | Moderate phototoxicity |
| 1: | Slight phototoxicity |

-continued

Injury rating:

0: No phototoxicity

TABLE 2

| Compound No. | Concentration of spray liquid (ppm) | Control value (%) | Degree of phytotoxicity |
|---|---|---|---|
| 1 | 200 | 89 | 0 |
| 2 | " | 84 | 0 |
| 3 | " | 100 | 0 |
| 4 | " | 100 | 0 |
| 5 | " | 83 | 0 |
| 6 | " | 93 | 0 |
| 7 | " | 100 | 0 |
| 8 | " | 99 | 0 |
| 10 | " | 80 | 0 |
| 11 | " | 100 | 0 |
| 12 | " | 87 | 0 |
| 13 | " | 82 | 0 |
| 14 | " | 100 | 0 |
| 15 | " | 100 | 0 |
| 17 | " | 75 | 0 |
| 19 | " | 75 | 0 |
| 20 | " | 86 | 0 |
| 22 | " | 94 | 0 |
| 23 | " | 100 | 0 |
| 24 | " | 100 | 0 |
| 25 | " | 75 | 0 |
| 26 | " | 100 | 0 |
| 27 | " | 80 | 0 |
| 28 | " | 75 | 0 |
| 29 | " | 91 | 0 |
| 30 | " | 85 | 0 |
| 31 | " | 75 | 0 |
| 32 | " | 100 | 0 |
| 34 | " | 87 | 0 |
| 35 | " | 76 | 0 |
| 36 | " | 100 | 0 |
| 37 | " | 80 | 0 |
| 38 | " | 91 | 0 |
| 39 | " | 100 | 0 |
| 40 | " | 79 | 0 |
| 41 | " | 95 | 0 |
| 42 | " | 89 | 0 |
| 44 | " | 81 | 0 |
| 45 | " | 75 | 0 |
| 47 | " | 75 | 0 |
| 48 | " | 100 | 0 |
| 49 | " | 94 | 0 |
| 51 | " | 100 | 0 |
| 52 | " | 100 | 0 |
| 53 | " | 75 | 0 |
| 54 | " | 84 | 0 |
| 55 | " | 97 | 0 |
| 56 | " | 75 | 0 |
| 58 | " | 100 | 0 |
| 59 | " | 100 | 0 |
| 61 | " | 100 | 0 |
| 62 | " | 100 | 0 |
| 63 | " | 100 | 0 |
| 65 | " | 100 | 0 |
| 66 | " | 75 | 0 |
| 67 | " | 97 | 0 |
| 69 | " | 100 | 0 |
| 70 | " | 88 | 0 |
| 71 | " | 100 | 0 |
| 72 | " | 75 | 0 |
| 73 | " | 100 | 0 |
| 74 | " | 88 | 0 |
| 75 | " | 96 | 0 |
| 76 | " | 75 | 0 |
| 77 | " | 81 | 0 |
| 78 | " | 79 | 0 |
| 79 | " | 75 | 0 |
| 80 | " | 75 | 0 |
| 81 | " | 80 | 0 |
| 82 | " | 77 | 0 |
| 83 | " | 75 | 0 |
| 84 | " | 75 | 0 |
| 86 | " | 87 | 0 |
| 87 | " | 95 | 0 |
| 88 | " | 85 | 0 |
| 89 | " | 75 | 0 |
| 90 | " | 83 | 0 |
| 91 | " | 99 | 0 |
| 92 | " | 98 | 0 |
| 93 | " | 100 | 0 |
| 94 | " | 75 | 0 |
| 96 | " | 86 | 0 |
| 98 | " | 95 | 0 |
| 99 | " | 75 | 0 |
| 100 | " | 83 | 0 |
| 103 | " | 82 | 0 |
| 104 | " | 75 | 0 |
| 105 | " | 75 | 0 |
| 107 | " | 93 | 0 |
| 108 | " | 75 | 0 |
| 109 | " | 82 | 0 |
| 110 | " | 75 | 0 |
| 111 | " | 75 | 0 |
| 112 | " | 85 | 0 |
| 113 | " | 96 | 0 |
| 114 | " | 100 | 0 |
| 115 | " | 100 | 0 |
| 116 | " | 100 | 0 |
| 117 | " | 100 | 0 |
| 118 | " | 100 | 0 |
| 119 | " | 93 | 0 |
| 120 | " | 100 | 0 |
| 121 | " | 75 | 0 |
| 122 | " | 94 | 0 |
| 123 | " | 100 | 0 |
| 124 | " | 100 | 0 |
| 125 | " | 100 | 0 |
| 127 | " | 100 | 0 |
| 128 | " | 100 | 0 |
| 129 | " | 100 | 0 |
| 130 | " | 90 | 0 |
| 131 | " | 100 | 0 |
| 132 | " | 100 | 0 |
| 133 | " | 93 | 0 |
| 134 | " | 86 | 0 |
| 135 | " | 78 | 0 |
| 136 | " | 75 | 0 |
| 137 | " | 100 | 0 |
| 138 | " | 75 | 0 |
| 139 | " | 100 | 0 |
| 140 | " | 100 | 0 |
| 141 | " | 81 | 0 |
| 142 | " | 100 | 0 |
| 143 | " | 100 | 0 |
| 144 | " | 100 | 0 |
| 145 | " | 100 | 0 |
| 146 | " | 100 | 0 |
| 147 | " | 100 | 0 |
| 148 | " | 100 | 0 |
| 149 | " | 100 | 0 |
| 151 | " | 100 | 0 |
| 152 | " | 99 | 0 |
| 153 | " | 100 | 0 |
| 155 | " | 100 | 0 |
| 156 | " | 100 | 0 |
| 157 | " | 100 | 0 |
| 158 | " | 100 | 0 |
| 159 | " | 71 | 0 |
| 160 | " | 82 | 0 |
| 162 | " | 83 | 0 |
| 164 | " | 97 | 0 |
| 166 | " | 77 | 0 |
| 167 | " | 93 | 0 |
| 168 | " | 87 | 0 |
| 169 | " | 78 | 0 |
| 170 | " | 87 | 0 |
| 171 | " | 98 | 0 |
| 172 | " | 100 | 0 |
| 173 | " | 100 | 0 |
| 174 | " | 84 | 0 |
| 175 | " | 80 | 0 |

TABLE 2-continued

| Compound No. | Concentration of spray liquid (ppm) | Control value (%) | Degree of phytotoxicity |
|---|---|---|---|
| 176 | " | 100 | 0 |
| 177 | " | 83 | 0 |
| 178 | " | 75 | 0 |
| 179 | " | 75 | 0 |
| 180 | " | 100 | 0 |
| 181 | " | 100 | 0 |
| 182 | " | 90 | 0 |
| 183 | " | 95 | 0 |
| 184 | " | 100 | 0 |
| 185 | " | 100 | 0 |
| 186 | " | 100 | 0 |
| 187 | " | 95 | 0 |
| 188 | " | 90 | 0 |
| 189 | " | 100 | 0 |
| 190 | " | 90 | 0 |
| 191 | " | 99 | 0 |
| 192 | " | 100 | 0 |
| 193 | " | 100 | 0 |
| 194 | " | 99 | 0 |
| 195 | " | 100 | 0 |
| 196 | " | 100 | 0 |
| 197 | " | 100 | 0 |
| 198 | " | 100 | 0 |
| 199 | " | 100 | 0 |
| 200 | " | 100 | 0 |
| 201 | " | 100 | 0 |
| 202 | " | 95 | 0 |
| 203 | " | 100 | 0 |
| 204 | " | 100 | 0 |
| 216 | " | 75 | 0 |
| 217 | " | 81 | 0 |
| 218 | " | 84 | 0 |
| 219 | " | 82 | 0 |
| 220 | " | 100 | 0 |
| 221 | " | 88 | 0 |
| 222 | " | 100 | 0 |
| 223 | " | 100 | 0 |
| 224 | " | 100 | 0 |
| 225 | " | 100 | 0 |
| 226 | " | 75 | 0 |
| 229 | " | 75 | 0 |
| 232 | " | 100 | 0 |
| 233 | " | 100 | 0 |
| 234 | " | 100 | 0 |
| 235 | " | 100 | 0 |
| 236 | " | 96 | 0 |
| 237 | " | 100 | 0 |
| 238 | " | 95 | 0 |
| 239 | " | 100 | 0 |
| 240 | " | 89 | 0 |
| 241 | " | 100 | 0 |
| 242 | " | 100 | 0 |
| 243 | " | 90 | 0 |
| 244 | " | 100 | 0 |
| 245 | " | 75 | 0 |
| 246 | " | 100 | 0 |
| 247 | " | 90 | 0 |
| 248 | " | 80 | 0 |
| 249 | " | 97 | 0 |
| 250 | " | 80 | 0 |
| 251 | " | 80 | 0 |
| 252 | " | 100 | 0 |
| 253 | " | 100 | 0 |
| 254 | " | 100 | 0 |
| 255 | " | 100 | 0 |
| 256 | " | 100 | 0 |
| 257 | " | 100 | 0 |
| 258 | " | 85 | 0 |
| 259 | " | 100 | 0 |
| 260 | " | 100 | 0 |
| 262 | " | 100 | 0 |
| 263 | " | 100 | 0 |
| 264 | " | 100 | 0 |
| 265 | " | 100 | 0 |
| 267 | " | 100 | 0 |
| 268 | " | 80 | 0 |
| 269 | " | 100 | 0 |
| 270 | " | 100 | 0 |
| 273 | " | 100 | 0 |
| 274 | " | 100 | 0 |
| 275 | " | 100 | 0 |
| 276 | " | 100 | 0 |
| 277 | " | 100 | 0 |
| 278 | " | 100 | 0 |
| 279 | " | 100 | 0 |
| 280 | " | 100 | 0 |
| 281 | " | 100 | 0 |
| 282 | " | 100 | 0 |
| 283 | " | 100 | 0 |
| 284 | " | 100 | 0 |
| 285 | " | 100 | 0 |
| 288 | " | 100 | 0 |
| 289 | " | 100 | 0 |
| 290 | " | 100 | 0 |
| 291 | " | 75 | 0 |
| 292 | " | 75 | 0 |
| 293 | " | 75 | 0 |
| 294 | " | 99 | 0 |
| 295 | " | 75 | 0 |
| 296 | " | 75 | 0 |
| 297 | " | 100 | 0 |
| 298 | " | 100 | 0 |
| 299 | " | 75 | 0 |
| 300 | " | 92 | 0 |
| 301 | " | 92 | 0 |
| 302 | " | 100 | 0 |
| 303 | " | 100 | 0 |
| 304 | " | 100 | 0 |
| 305 | " | 79 | 0 |
| 306 | " | 75 | 0 |
| 307 | " | 83 | 0 |
| 308 | " | 75 | 0 |
| 309 | " | 100 | 0 |
| 310 | " | 90 | 0 |
| 311 | " | 100 | 0 |
| 312 | " | 95 | 0 |
| 313 | " | 98 | 0 |
| 314 | " | 100 | 0 |
| 315 | " | 95 | 0 |
| 316 | " | 100 | 0 |
| 317 | " | 95 | 0 |
| 318 | " | 92 | 0 |
| 319 | " | 100 | 0 |
| 320 | " | 100 | 0 |
| 321 | " | 100 | 0 |
| 322 | " | 92 | 0 |
| 323 | " | 100 | 0 |
| 324 | " | 90 | 0 |
| 325 | " | 91 | 0 |
| 326 | " | 100 | 0 |
| 327 | " | 100 | 0 |
| 328 | " | 88 | 0 |
| 329 | " | 97 | 0 |
| 330 | " | 100 | 0 |
| 331 | " | 90 | 0 |
| 332 | " | 93 | 0 |
| 333 | " | 100 | 0 |
| 334 | " | 94 | 0 |
| 335 | " | 100 | 0 |
| 336 | " | 91 | 0 |
| 337 | " | 100 | 0 |
| 338 | " | 100 | 0 |
| 339 | " | 100 | 0 |
| 340 | " | 91 | 0 |
| 341 | " | 100 | 0 |
| 342 | " | 99 | 0 |
| 343 | " | 100 | 0 |
| Comparative chemical (EDDP) | " | 95 | 0 |

| Compound No. | Concentration of spray liquid (ppm) | Control value (%) | Degree of phytotoxicity |
|---|---|---|---|
| Non-treated | — | 0 | — |

(Note)

EDDP: 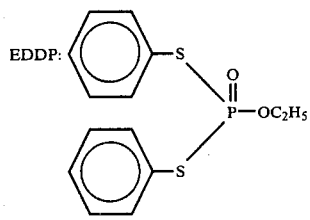

TEST EXAMPLE 2

Test for Control Effect on Paddy Rice Brown Spot

Over the 4th-true leaf stage seedlings of paddy rice (variety: Asahi) soil cultured in a porcelain pot of 9 cm in diameter in a greenhouse was sprayed a test liquid prepared by diluting the compound to a predetermined concentration with water. One day after completion of the spraying of the test liquid, the seedlings were inoculated with a spore suspension of rice brown spot fungus (*Cochliobolus miyabeanus*). Five (5) days after the inoculation, the number of lesions per leaf of the 4-stage true leaves was investigated and the preventive value was calculated on the basis of the following equation. Furthermore, the phytotoxic activity against the paddy rice plant of the test compound was investigated according to the same procedure as in Test Example 1. The results obtained are as shown in Table 3.

$$\text{Control value (\%)} = \left(1 - \frac{\text{Number of lesions in treated plot}}{\text{Number of lesions in blank plot}}\right) \times 100$$

TABLE 3

| Compound No. | Concentration of spray liquid (ppm) | Control value (%) | Degree of phytotoxicity |
|---|---|---|---|
| 2 | 500 | 100 | 0 |
| 3 | " | 100 | 0 |
| 4 | " | 100 | 0 |
| 5 | " | 100 | 0 |
| 6 | " | 100 | 0 |
| 7 | " | 100 | 0 |
| 8 | " | 94 | 0 |
| 10 | " | 100 | 0 |
| 15 | " | 83 | 0 |
| 16 | " | 75 | 0 |
| 17 | " | 93 | 0 |
| 18 | " | 100 | 0 |
| 19 | " | 100 | 0 |
| 20 | " | 100 | 0 |
| 21 | " | 100 | 0 |
| 22 | " | 100 | 0 |
| 23 | " | 100 | 0 |
| 24 | " | 100 | 0 |
| 25 | " | 92 | 0 |
| 26 | " | 85 | 0 |
| 27 | " | 89 | 0 |
| 29 | " | 100 | 0 |
| 30 | " | 100 | 0 |
| 31 | " | 93 | 0 |
| 32 | " | 75 | 0 |
| 36 | " | 92 | 0 |
| 37 | " | 75 | 0 |
| 44 | " | 79 | 0 |
| 49 | " | 100 | 0 |
| 50 | " | 100 | 0 |
| 51 | " | 91 | 0 |
| 52 | " | 100 | 0 |
| 54 | " | 90 | 0 |
| 55 | " | 100 | 0 |
| 56 | " | 100 | 0 |
| 58 | " | 98 | 0 |
| 59 | " | 100 | 0 |
| 62 | " | 100 | 0 |
| 63 | " | 100 | 0 |
| 64 | " | 91 | 0 |
| 65 | " | 100 | 0 |
| 68 | " | 100 | 0 |
| 69 | " | 100 | 0 |
| 71 | " | 100 | 0 |
| 74 | " | 83 | 0 |
| 77 | " | 75 | 0 |
| 85 | " | 75 | 0 |
| 86 | " | 75 | 0 |
| 95 | " | 75 | 0 |
| 97 | " | 75 | 0 |
| 103 | " | 88 | 0 |
| 106 | " | 75 | 0 |
| 113 | " | 100 | 0 |
| 114 | " | 100 | 0 |
| 115 | " | 100 | 0 |
| 116 | " | 100 | 0 |
| 118 | " | 100 | 0 |
| 119 | " | 90 | 0 |
| 120 | " | 100 | 0 |
| 123 | " | 100 | 0 |
| 124 | " | 100 | 0 |
| 125 | " | 100 | 0 |
| 126 | " | 100 | 0 |
| 128 | " | 100 | 0 |
| 129 | " | 100 | 0 |
| 131 | " | 100 | 0 |
| 132 | " | 100 | 0 |
| 133 | " | 100 | 0 |
| 134 | " | 100 | 0 |
| 135 | " | 88 | 0 |
| 136 | " | 92 | 0 |
| 139 | " | 100 | 0 |
| 140 | " | 100 | 0 |
| 141 | " | 100 | 0 |
| 142 | " | 100 | 0 |
| 143 | " | 100 | 0 |
| 144 | " | 100 | 0 |
| 145 | " | 100 | 0 |
| 146 | " | 100 | 0 |
| 147 | " | 100 | 0 |
| 148 | " | 100 | 0 |
| 149 | " | 100 | 0 |
| 155 | " | 100 | 0 |
| 159 | " | 96 | 0 |
| 160 | " | 96 | 0 |
| 161 | " | 100 | 0 |
| 162 | " | 99 | 0 |
| 163 | " | 100 | 0 |
| 164 | " | 100 | 0 |
| 165 | " | 99 | 0 |
| 167 | " | 73 | 0 |
| 170 | " | 82 | 0 |
| 171 | " | 80 | 0 |
| 172 | " | 84 | 0 |
| 181 | " | 85 | 0 |
| 182 | " | 95 | 0 |
| 183 | " | 100 | 0 |
| 184 | " | 100 | 0 |
| 185 | " | 100 | 0 |
| 186 | " | 90 | 0 |
| 187 | " | 100 | 0 |
| 188 | " | 90 | 0 |
| 189 | " | 100 | 0 |
| 190 | " | 99 | 0 |
| 191 | " | 100 | 0 |
| 192 | " | 100 | 0 |
| 193 | " | 100 | 0 |

TABLE 3-continued

| Compound No. | Concentration of spray liquid (ppm) | Control value (%) | Degree of phytotoxicity |
|---|---|---|---|
| 194 | " | 90 | 0 |
| 195 | " | 100 | 0 |
| 196 | " | 95 | 0 |
| 197 | " | 90 | 0 |
| 198 | " | 100 | 0 |
| 199 | " | 100 | 0 |
| 200 | " | 100 | 0 |
| 201 | " | 100 | 0 |
| 202 | " | 100 | 0 |
| 203 | " | 100 | 0 |
| 204 | " | 100 | 0 |
| 205 | " | 93 | 0 |
| 207 | " | 95 | 0 |
| 208 | " | 97 | 0 |
| 209 | " | 75 | 0 |
| 210 | " | 75 | 0 |
| 212 | " | 84 | 0 |
| 213 | " | 91 | 0 |
| 214 | " | 75 | 0 |
| 215 | " | 96 | 0 |
| 216 | " | 100 | 0 |
| 217 | " | 92 | 0 |
| 218 | " | 97 | 0 |
| 211 | " | 88 | 0 |
| 212 | " | 100 | 0 |
| 213 | " | 100 | 0 |
| 214 | " | 100 | 0 |
| 215 | " | 100 | 0 |
| 216 | " | 100 | 0 |
| 217 | " | 75 | 0 |
| 229 | " | 75 | 0 |
| 231 | " | 100 | 0 |
| 232 | " | 100 | 0 |
| 233 | " | 100 | 0 |
| 234 | " | 100 | 0 |
| 235 | " | 100 | 0 |
| 236 | " | 95 | 0 |
| 237 | " | 100 | 0 |
| 238 | " | 100 | 0 |
| 239 | " | 100 | 0 |
| 240 | " | 96 | 0 |
| 241 | " | 98 | 0 |
| 242 | " | 100 | 0 |
| 243 | " | 98 | 0 |
| 244 | " | 100 | 0 |
| 246 | " | 100 | 0 |
| 247 | " | 100 | 0 |
| 248 | " | 100 | 0 |
| 249 | " | 100 | 0 |
| 250 | " | 100 | 0 |
| 251 | " | 100 | 0 |
| 252 | " | 95 | 0 |
| 254 | " | 95 | 0 |
| 255 | " | 100 | 0 |
| 256 | " | 100 | 0 |
| 257 | " | 90 | 0 |
| 258 | " | 90 | 0 |
| 262 | " | 100 | 0 |
| 263 | " | 93 | 0 |
| 267 | " | 100 | 0 |
| 270 | " | 90 | 0 |
| 271 | " | 90 | 0 |
| 274 | " | 85 | 0 |
| 275 | " | 90 | 0 |
| 276 | " | 90 | 0 |
| 279 | " | 90 | 0 |
| 280 | " | 100 | 0 |
| 281 | " | 90 | 0 |
| 282 | " | 100 | 0 |
| 283 | " | 100 | 0 |
| 284 | " | 95 | 0 |
| 288 | " | 100 | 0 |
| 289 | " | 100 | 0 |
| 291 | " | 100 | 0 |
| 294 | " | 100 | 0 |
| 295 | " | 100 | 0 |
| 297 | " | 97 | 0 |
| 298 | " | 100 | 0 |
| 300 | " | 95 | 0 |
| 301 | " | 100 | 0 |
| 302 | " | 100 | 0 |
| 303 | " | 86 | 0 |
| 304 | " | 100 | 0 |
| 305 | " | 100 | 0 |
| 306 | " | 100 | 0 |
| 307 | " | 100 | 0 |
| 308 | " | 100 | 0 |
| 309 | " | 100 | 0 |
| 310 | " | 100 | 0 |
| 311 | " | 100 | 0 |
| 312 | " | 100 | 0 |
| 313 | " | 100 | 0 |
| 314 | " | 100 | 0 |
| 315 | " | 100 | 0 |
| 316 | " | 100 | 0 |
| 317 | " | 100 | 0 |
| 318 | " | 92 | 0 |
| 319 | " | 94 | 0 |
| 320 | " | 100 | 0 |
| 321 | " | 100 | 0 |
| 322 | " | 100 | 0 |
| 323 | " | 93 | 0 |
| 324 | " | 100 | 0 |
| 325 | " | 100 | 0 |
| 326 | " | 94 | 0 |
| 327 | " | 100 | 0 |
| 328 | " | 100 | 0 |
| 329 | " | 91 | 0 |
| 330 | " | 100 | 0 |
| 331 | " | 97 | 0 |
| 332 | " | 100 | 0 |
| 333 | " | 100 | 0 |
| 334 | " | 100 | 0 |
| 335 | " | 100 | 0 |
| 336 | " | 99 | 0 |
| 337 | " | 100 | 0 |
| 338 | " | 98 | 0 |
| 339 | " | 100 | 0 |
| 340 | " | 100 | 0 |
| 341 | " | 100 | 0 |
| 342 | " | 100 | 0 |
| 343 | " | 100 | 0 |
| Comparative chemical (Triazine) | " | 90 | 0 |
| Non-treated | — | 0 | — |

(Note)

Triazine:

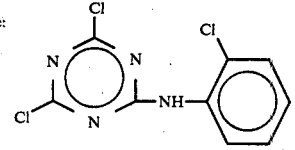

TEST EXAMPLE 3

Test for Control Effect of Paddy Rice Sheath Blight

Over the 6th-leaf stage seedlings of paddy rice soil cultured in a porcelain pot of 9 cm in diameter was sprayed 40 ml per 3 pots of a test liquid of the compound having a predetermined concentration, and the seedlings thus treated were allowed to stand in a highly humidified glass chamber for weathering. One day after the spraying of the test liquid, inoculation conducted by patching each seedling at the second leaf sheath position with an agar disc obtained by perforating by means of a cork borer of 5 mm in diameter the edge of a colony of the pathogenic fungus (*Pellicularia sasakii*), which had previously been cultured (at 27° C. for 48 hours) on a potato sucrose agar medium, and the thus inoculated seedlings were kept in a moist chamber (at 95–100% relative humidity and 28° C.). Four days after the inoculation, outbreak of the disease was observed by investigating the lesion length per seedling and the preventive value (%) was obtained in comparison with the blank plot, according to the following equation.

$$\text{Control value (\%)} = \left(1 - \frac{\text{Lesion length in treated plot}}{\text{Lesion length in blank plot}}\right) \times 100$$

The test results obtained are as shown in Table 4.

TABLE 4

| Compound No. | Concentration of spray liquid (ppm) | Control value (%) | Degree of phytotoxicity |
|---|---|---|---|
| 4 | 500 | 100 | 0 |
| 6 | " | 100 | 0 |
| 7 | " | 100 | 0 |
| 8 | " | 83 | 0 |
| 17 | " | 75 | 0 |
| 24 | " | 100 | 0 |
| 27 | " | 100 | 0 |
| 29 | " | 75 | 0 |
| 32 | " | 100 | 0 |
| 34 | " | 75 | 0 |
| 35 | " | 100 | 0 |
| 37 | " | 78 | 0 |
| 38 | " | 100 | 0 |
| 43 | " | 100 | 0 |
| 45 | " | 100 | 0 |
| 47 | " | 75 | 0 |
| 48 | " | 75 | 0 |
| 52 | " | 96 | 0 |
| 54 | " | 75 | 0 |
| 55 | " | 90 | 0 |
| 59 | " | 99 | 0 |
| 65 | " | 75 | 0 |
| 67 | " | 80 | 0 |
| 73 | " | 75 | 0 |
| 87 | " | 75 | 0 |
| 89 | " | 75 | 0 |
| 93 | " | 75 | 0 |
| 101 | " | 75 | 0 |
| 102 | " | 75 | 0 |
| 127 | " | 75 | 0 |
| 129 | " | 75 | 0 |
| 131 | " | 95 | 0 |
| 133 | " | 75 | 0 |
| 134 | " | 79 | 0 |
| 135 | " | 94 | 0 |
| 137 | " | 75 | 0 |
| 140 | " | 75 | 0 |
| 144 | " | 100 | 0 |
| 145 | " | 75 | 0 |
| 151 | " | 85 | 0 |
| 153 | " | 92 | 0 |
| 294 | " | 75 | 0 |
| 295 | " | 94 | 0 |
| 296 | " | 83 | 0 |
| Comparative chemical (Neoasozine) | 65 | 90 | 0 |
| Non-treated | — | 0 | — |

(Note)
Neoasozine: Ammonium iron methanearsonate

TEST EXAMPLE 4

Test for Control Effect on Tomato Late Blight

Over the young seedlings of tomato (variety: Sekaiichi, the second true leaf stage seedlings) soil cultured in a porcelain pot of 9 cm in diameter in a greenhouse was sprayed by means of a pressure sprayer a test liquid prepared by diluting to a predetermined concentration with water a wettable powder prepared according to the general procedure of Example 25. Three days after completion of the spraying of the test liquid, the leaves of treated seedlings were inoculated by dropping the zoosporangia suspension of pathogenic fungus (*Phytophthora infestans*) with a needle injector, said pathogenic fungus having previously been cultured on potato tubers at 20° C. for 3 days. After completion of the inoculation, the thus treated seedlings were kept in a humidified chamber (at 95-98% relative humidity), and three days thereafter, outbreak of the disease was observed and the control value (%) was calculated according to the following equation. Furthermore, the phytotoxicity against the tomato plant of the test compound was investigated according to the same procedure as in Test Example 1.

$$\text{Infection ratio (\%)} = \left(1 - \frac{\text{Number of leaves infected}}{\text{Number of leaves inoculated}}\right) \times 100$$

$$\text{Control value (\%)} = \left(1 - \frac{\text{Infection ratio in treated plot}}{\text{Infection ratio in blank plot}}\right) \times 100$$

The results obtained are as shown in Table 5.

TABLE 5

| Compound No. | Concentration of spray liquid (ppm) | Control value (%) | Degree of phytotoxicity |
|---|---|---|---|
| 2 | 500 | 100 | 0 |
| 3 | " | 93 | 0 |
| 4 | " | 100 | 0 |
| 5 | " | 100 | 0 |
| 7 | " | 100 | 0 |
| 8 | " | 100 | 0 |
| 10 | " | 100 | 0 |
| 13 | " | 92 | 0 |
| 15 | " | 84 | 0 |
| 17 | " | 78 | 0 |
| 18 | " | 100 | 0 |
| 19 | " | 100 | 0 |
| 20 | " | 100 | 0 |
| 21 | " | 100 | 0 |
| 22 | " | 100 | 0 |
| 23 | " | 100 | 0 |
| 24 | " | 100 | 0 |
| 27 | " | 100 | 0 |
| 29 | " | 100 | 0 |
| 30 | " | 100 | 0 |
| 32 | " | 75 | 0 |
| 41 | " | 75 | 0 |
| 42 | " | 92 | 0 |
| 45 | " | 81 | 0 |
| 52 | " | 100 | 0 |
| 53 | " | 96 | 0 |
| 54 | " | 100 | 0 |
| 55 | " | 100 | 0 |
| 56 | " | 84 | 0 |
| 58 | " | 100 | 0 |
| 59 | " | 100 | 0 |
| 61 | " | 88 | 0 |
| 63 | " | 100 | 0 |
| 64 | " | 96 | 0 |
| 65 | " | 100 | 0 |
| 66 | " | 85 | 0 |
| 67 | " | 75 | 0 |
| 69 | " | 86 | 0 |
| 71 | " | 100 | 0 |
| 72 | " | 98 | 0 |
| 75 | " | 100 | 0 |
| 76 | " | 100 | 0 |
| 77 | " | 100 | 0 |
| 81 | " | 100 | 0 |

TABLE 5-continued

| Compound No. | Concentration of spray liquid (ppm) | Control value (%) | Degree of phytotoxicity |
|---|---|---|---|
| 82 | ″ | 91 | 0 |
| 110 | ″ | 80 | 0 |
| 113 | ″ | 100 | 0 |
| 114 | ″ | 96 | 0 |
| 115 | ″ | 100 | 0 |
| 116 | ″ | 100 | 0 |
| 117 | ″ | 100 | 0 |
| 118 | ″ | 100 | 0 |
| 119 | ″ | 100 | 0 |
| 120 | ″ | 100 | 0 |
| 125 | ″ | 100 | 0 |
| 126 | ″ | 100 | 0 |
| 128 | ″ | 100 | 0 |
| 129 | ″ | 75 | 0 |
| 131 | ″ | 100 | 0 |
| 132 | ″ | 100 | 0 |
| 133 | ″ | 100 | 0 |
| 134 | ″ | 100 | 0 |
| 135 | ″ | 100 | 0 |
| 136 | ″ | 100 | 0 |
| 139 | ″ | 75 | 0 |
| 141 | ″ | 100 | 0 |
| 142 | ″ | 75 | 0 |
| 143 | ″ | 100 | 0 |
| 144 | ″ | 100 | 0 |
| 145 | ″ | 100 | 0 |
| 146 | ″ | 100 | 0 |
| 147 | ″ | 100 | 0 |
| 148 | ″ | 100 | 0 |
| 149 | ″ | 100 | 0 |
| 157 | ″ | 90 | 0 |
| 159 | ″ | 99 | 0 |
| 160 | ″ | 75 | 0 |
| 162 | ″ | 100 | 0 |
| 163 | ″ | 80 | 0 |
| 164 | ″ | 100 | 0 |
| 165 | ″ | 100 | 0 |
| 169 | ″ | 91 | 0 |
| 171 | ″ | 75 | 0 |
| 173 | ″ | 77 | 0 |
| 174 | ″ | 75 | 0 |
| 177 | ″ | 93 | 0 |
| 178 | ″ | 83 | 0 |
| 180 | ″ | 100 | 0 |
| 181 | ″ | 100 | 0 |
| 182 | ″ | 95 | 0 |
| 183 | ″ | 100 | 0 |
| 184 | ″ | 100 | 0 |
| 185 | ″ | 100 | 0 |
| 187 | ″ | 100 | 0 |
| 188 | ″ | 100 | 0 |
| 190 | ″ | 96 | 0 |
| 191 | ″ | 100 | 0 |
| 192 | ″ | 90 | 0 |
| 193 | ″ | 100 | 0 |
| 194 | ″ | 100 | 0 |
| 196 | ″ | 96 | 0 |
| 197 | ″ | 100 | 0 |
| 198 | ″ | 100 | 0 |
| 199 | ″ | 100 | 0 |
| 200 | ″ | 100 | 0 |
| 202 | ″ | 100 | 0 |
| 203 | ″ | 100 | 0 |
| 204 | ″ | 100 | 0 |
| 205 | ″ | 75 | 0 |
| 207 | ″ | 77 | 0 |
| 208 | ″ | 75 | 0 |
| 210 | ″ | 82 | 0 |
| 211 | ″ | 75 | 0 |
| 212 | ″ | 94 | 0 |
| 214 | ″ | 98 | 0 |
| 215 | ″ | 88 | 0 |
| 216 | ″ | 99 | 0 |
| 217 | ″ | 100 | 0 |
| 218 | ″ | 77 | 0 |
| 219 | ″ | 91 | 0 |
| 220 | ″ | 100 | 0 |
| 222 | ″ | 100 | 0 |
| 223 | ″ | 75 | 0 |
| 224 | ″ | 99 | 0 |
| 225 | ″ | 89 | 0 |
| 226 | ″ | 100 | 0 |
| 227 | ″ | 75 | 0 |
| 229 | ″ | 96 | 0 |
| 231 | ″ | 100 | 0 |
| 233 | ″ | 76 | 0 |
| 234 | ″ | 95 | 0 |
| 235 | ″ | 100 | 0 |
| 236 | ″ | 100 | 0 |
| 237 | ″ | 95 | 0 |
| 238 | ″ | 90 | 0 |
| 239 | ″ | 100 | 0 |
| 240 | ″ | 100 | 0 |
| 241 | ″ | 96 | 0 |
| 242 | ″ | 100 | 0 |
| 243 | ″ | 90 | 0 |
| 244 | ″ | 100 | 0 |
| 246 | ″ | 100 | 0 |
| 247 | ″ | 100 | 0 |
| 248 | ″ | 100 | 0 |
| 249 | ″ | 100 | 0 |
| 251 | ″ | 100 | 0 |
| 252 | ″ | 100 | 0 |
| 253 | ″ | 100 | 0 |
| 254 | ″ | 100 | 0 |
| 255 | ″ | 100 | 0 |
| 256 | ″ | 90 | 0 |
| 257 | ″ | 90 | 0 |
| 258 | ″ | 95 | 0 |
| 259 | ″ | 100 | 0 |
| 262 | ″ | 90 | 0 |
| 264 | ″ | 90 | 0 |
| 265 | ″ | 100 | 0 |
| 266 | ″ | 90 | 0 |
| 267 | ″ | 100 | 0 |
| 270 | ″ | 100 | 0 |
| 271 | ″ | 100 | 0 |
| 274 | ″ | 100 | 0 |
| 275 | ″ | 100 | 0 |
| 276 | ″ | 100 | 0 |
| 280 | ″ | 100 | 0 |
| 281 | ″ | 100 | 0 |
| 282 | ″ | 100 | 0 |
| 283 | ″ | 100 | 0 |
| 284 | ″ | 100 | 0 |
| 286 | ″ | 90 | 0 |
| 288 | ″ | 100 | 0 |
| 289 | ″ | 100 | 0 |
| 291 | ″ | 90 | 0 |
| 292 | ″ | 100 | 0 |
| 294 | ″ | 100 | 0 |
| 295 | ″ | 100 | 0 |
| 297 | ″ | 100 | 0 |
| 298 | ″ | 100 | 0 |
| 301 | ″ | 100 | 0 |
| 302 | ″ | 100 | 0 |
| 303 | ″ | 100 | 0 |
| 304 | ″ | 100 | 0 |
| 305 | ″ | 100 | 0 |
| 306 | ″ | 100 | 0 |
| 307 | ″ | 100 | 0 |
| 308 | ″ | 100 | 0 |
| 309 | ″ | 95 | 0 |
| 310 | ″ | 100 | 0 |
| 311 | ″ | 95 | 0 |
| 312 | ″ | 100 | 0 |
| 314 | ″ | 100 | 0 |
| 315 | ″ | 100 | 0 |
| 316 | ″ | 100 | 0 |
| 318 | ″ | 100 | 0 |
| 320 | ″ | 100 | 0 |
| 321 | ″ | 100 | 0 |
| 322 | ″ | 100 | 0 |
| 324 | ″ | 100 | 0 |
| 326 | ″ | 100 | 0 |
| 328 | ″ | 100 | 0 |
| 329 | ″ | 100 | 0 |
| 330 | ″ | 90 | 0 |

TABLE 5-continued

| Compound No. | Concentration of spray liquid (ppm) | Control value (%) | Degree of phytotoxicity |
|---|---|---|---|
| 331 | " | 95 | 0 |
| 332 | " | 100 | 0 |
| 333 | " | 100 | 0 |
| 335 | " | 100 | 0 |
| 336 | " | 100 | 0 |
| 337 | " | 99 | 0 |
| 338 | " | 100 | 0 |
| 339 | " | 100 | 0 |
| 340 | " | 100 | 0 |
| 341 | " | 100 | 0 |
| 342 | " | 100 | 0 |
| 343 | " | 100 | 0 |
| Comparative chemical (TPN) | " | 95 | 0 |
| Non-treated | — | 0 | — |

(Note) TPN:

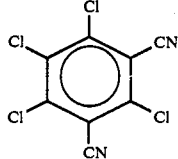

TEST EXAMPLE 5

Test for Control Effect on Haricot Sclerotinia Rot

Over the seedlings of haricot (variety: Taisho Kintoki) soil cultured in a porcelain pot of 9 cm in diameter in a greenhouse was sprayed, when the first rue leaf completely developed, 15 ml each per pot of a test liquid of the compound diluted with water to a predetermined concentration. On the following day, the first trifoliate leaf was cut off and the each leaflet of trifoliate leaf were placed in a 15 cm petri dish kept under moist conditions by placeing a wet filter paper thereon and were inoculated on the center portion of each leaflet with a fungus-containing agar segment obtained by perforating by means of a cork borer of 8 mm in diameter an edge of a colony of a haricot sclerotinia rot (*Sclerotinia sclerotiorum*) cultured previously at 20° C. for 2 days in PSA medium. Three days after inoculation, the lesion diameter formed was measured by means of slide calipers and the control value (%) was obtained according to the following equation. Furthermore, the phytotoxicity against the haricot plant of the test compound was investigated according to the same procedure as in Test Example 1.

Control value (%)=(1−B/A)×100

A=Lesion length in blank plot—diameter of inoculation source (8 mm)
B=Lesion length in treated plot—diameter of inoculation source (8 mm)

The results obtained are as shown in Table 6.

TABLE 6

| Compound No. | Concentration of spray liquid (ppm) | Control value (%) | Degree of phytotoxicity |
|---|---|---|---|
| 1 | 200 | 81 | 0 |
| 3 | " | 100 | 0 |
| 4 | " | 75 | 0 |
| 5 | " | 100 | 0 |
| 6 | " | 94 | 0 |
| 7 | " | 100 | 0 |
| 17 | " | 72 | 0 |
| 19 | " | 90 | 0 |
| 20 | " | 75 | 0 |
| 22 | " | 95 | 0 |
| 23 | " | 81 | 0 |
| 25 | " | 95 | 0 |
| 27 | " | 100 | 0 |
| 29 | " | 75 | 0 |
| 30 | " | 78 | 0 |
| 33 | " | 75 | 0 |
| 45 | " | 75 | 0 |
| 51 | " | 75 | 0 |
| 52 | " | 79 | 0 |
| 65 | " | 75 | 0 |
| 67 | " | 75 | 0 |
| 89 | " | 75 | 0 |
| 96 | " | 100 | 0 |
| 103 | " | 79 | 0 |
| 113 | " | 100 | 0 |
| 114 | " | 93 | 0 |
| 115 | " | 100 | 0 |
| 116 | " | 100 | 0 |
| 118 | " | 100 | 0 |
| 119 | " | 75 | 0 |
| 120 | " | 75 | 0 |
| 123 | " | 100 | 0 |
| 124 | " | 100 | 0 |
| 125 | " | 100 | 0 |
| 127 | " | 75 | 0 |
| 128 | " | 100 | 0 |
| 131 | " | 100 | 0 |
| 132 | " | 100 | 0 |
| 134 | " | 100 | 0 |
| 135 | " | 100 | 0 |
| 136 | " | 100 | 0 |
| 139 | " | 100 | 0 |
| 140 | " | 100 | 0 |
| 142 | " | 100 | 0 |
| 146 | " | 82 | 0 |
| 205 | " | 75 | 0 |
| 206 | " | 75 | 0 |
| 216 | " | 75 | 0 |
| 217 | " | 100 | 0 |
| 218 | " | 84 | 0 |
| 219 | " | 75 | 0 |
| 220 | " | 100 | 0 |
| 221 | " | 100 | 0 |
| 223 | " | 86 | 0 |
| 224 | " | 100 | 0 |
| 225 | " | 75 | 0 |
| 226 | " | 75 | 0 |
| 234 | " | 80 | 0 |
| 235 | " | 75 | 0 |
| 241 | " | 75 | 0 |
| 243 | " | 80 | 0 |
| 244 | " | 80 | 0 |
| 246 | " | 100 | 0 |
| 247 | " | 100 | 0 |
| 248 | " | 100 | 0 |
| 249 | " | 100 | 0 |
| 252 | " | 90 | 0 |
| 254 | " | 90 | 0 |
| 280 | " | 90 | 0 |
| 287 | " | 90 | 0 |
| 304 | " | 98 | 0 |
| Comparative chemical (Thiophanate-methyl) | " | 70 | 0 |
| Non-treated | — | 0 | — |

(Note)
Thiophanate-methyl:

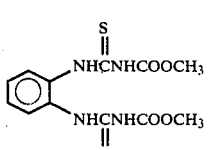

TEST EXAMPLE 6

Test for Control Effect on Cucumber Downy Mildew

The young seedlings of cucumber (variety: Sagami Hanjiro, the first true leaf stage seedlings) cultivated in a greenhouse were placed on a turn table, and thereover was sprayed by means of a spray gun a test liquid of a wettable powder prepared according to the general procedure of Example 25 and diluted with water to a predetermined concentration. On the following day, the seedlings were inoculated by atomizing technique with a suspension of spores of a cucumber downy mildew fungus (*Pseudoperonospora cubensis*) which had been sporulated on the affected leaves of cucumber were brushed away into deionized water containing 50 ppm of Tween 20 (polyoxyethylene sorbitan monolaurate), so that the spore concentration in the suspension became 20–30 spores per unit visible field under a microscope of 150 magnifications. After keeping in a fumidified chamber at 20° C. for 24 hours, the inoculated seedlings were placed in a greenhouse to accelerate infection. Five days after the inoculation, percent lesion area of each leaf was investigated and the control value (%) in a treated plot was calculated in comparison with a blank plot, according to the following equation.

$$\text{Control value (\%)} = \left(1 - \frac{\text{Percent lesion area in treated plot}}{\text{Percent lesion area in blank plot}}\right) \times 100$$

The results obtained are as shown in Table 7.

TABLE 7

| Compound No. | Concentration of spray liquid (ppm) | Control value (%) | Degree of phytotoxicity |
|---|---|---|---|
| 1 | 500 | 100 | 0 |
| 2 | " | 100 | 0 |
| 5 | " | 100 | 0 |
| 6 | " | 100 | 0 |
| 10 | " | 100 | 0 |
| 18 | " | 78 | 0 |
| 19 | " | 100 | 0 |
| 20 | " | 100 | 0 |
| 21 | " | 100 | 0 |
| 22 | " | 100 | 0 |
| 23 | " | 100 | 0 |
| 24 | " | 100 | 0 |
| 25 | " | 100 | 0 |
| 26 | " | 100 | 0 |
| 29 | " | 100 | 0 |
| 30 | " | 100 | 0 |
| 31 | " | 100 | 0 |
| 32 | " | 100 | 0 |
| 49 | " | 100 | 0 |
| 50 | " | 100 | 0 |
| 51 | " | 100 | 0 |
| 52 | " | 100 | 0 |
| 53 | " | 100 | 0 |
| 54 | " | 100 | 0 |
| 56 | " | 100 | 0 |
| 57 | " | 100 | 0 |
| 58 | " | 100 | 0 |
| 59 | " | 100 | 0 |
| 60 | " | 100 | 0 |
| 61 | " | 100 | 0 |
| 62 | " | 100 | 0 |
| 63 | " | 100 | 0 |
| 64 | " | 100 | 0 |
| 65 | " | 100 | 0 |
| 66 | " | 100 | 0 |
| 67 | " | 100 | 0 |
| 68 | " | 100 | 0 |
| 69 | " | 100 | 0 |
| 70 | " | 100 | 0 |
| 71 | " | 100 | 0 |
| 72 | " | 100 | 0 |
| 73 | " | 94 | 0 |
| 74 | " | 100 | 0 |
| 75 | " | 100 | 0 |
| 76 | " | 100 | 0 |
| 77 | " | 90 | 0 |
| 78 | " | 97 | 0 |
| 114 | " | 100 | 0 |
| 122 | " | 100 | 0 |
| 129 | " | 100 | 0 |
| 137 | " | 100 | 0 |
| 143 | " | 100 | 0 |
| 144 | " | 100 | 0 |
| 145 | " | 100 | 0 |
| 146 | " | 100 | 0 |
| 147 | " | 100 | 0 |
| 148 | " | 100 | 0 |
| 149 | " | 100 | 0 |
| 160 | " | 100 | 0 |
| 163 | " | 100 | 0 |
| 178 | " | 100 | 0 |
| 179 | " | 100 | 0 |
| 166 | " | 100 | 0 |
| 169 | " | 85 | 0 |
| 170 | " | 93 | 0 |
| 174 | " | 87 | 0 |
| 175 | " | 80 | 0 |
| 205 | " | 100 | 0 |
| 207 | " | 100 | 0 |
| 208 | " | 100 | 0 |
| 209 | " | 100 | 0 |
| 211 | " | 100 | 0 |
| 213 | " | 100 | 0 |
| 214 | " | 90 | 0 |
| 215 | " | 100 | 0 |
| 217 | " | 100 | 0 |
| 219 | " | 100 | 0 |
| 221 | " | 100 | 0 |
| 222 | " | 100 | 0 |
| 223 | " | 100 | 0 |
| 225 | " | 100 | 0 |
| 227 | " | 100 | 0 |
| 228 | " | 100 | 0 |
| 229 | " | 100 | 0 |
| 230 | " | 100 | 0 |
| 231 | " | 100 | 0 |
| 232 | " | 100 | 0 |
| 233 | " | 100 | 0 |
| 234 | " | 100 | 0 |
| 236 | " | 100 | 0 |
| 238 | " | 100 | 0 |
| 240 | " | 100 | 0 |
| 242 | " | 100 | 0 |
| 244 | " | 100 | 0 |
| 245 | " | 100 | 0 |
| 252 | " | 100 | 0 |
| 253 | " | 100 | 0 |
| 254 | " | 100 | 0 |
| 255 | " | 100 | 0 |
| 256 | " | 100 | 0 |
| 257 | " | 100 | 0 |
| 258 | " | 100 | 0 |
| 259 | " | 100 | 0 |
| 260 | " | 100 | 0 |
| 262 | " | 100 | 0 |
| 263 | " | 100 | 0 |
| 264 | " | 100 | 0 |
| 265 | " | 90 | 0 |
| 267 | " | 100 | 0 |
| 268 | " | 100 | 0 |
| 269 | " | 100 | 0 |
| 270 | " | 100 | 0 |
| 271 | " | 100 | 0 |
| 272 | " | 100 | 0 |
| 273 | " | 95 | 0 |
| 274 | " | 90 | 0 |

TABLE 7-continued

| Compound No. | Concentration of spray liquid (ppm) | Control value (%) | Degree of phytotoxicity |
|---|---|---|---|
| 275 | " | 100 | 0 |
| 276 | " | 100 | 0 |
| 278 | " | 100 | 0 |
| 279 | " | 100 | 0 |
| 280 | " | 100 | 0 |
| 281 | " | 100 | 0 |
| 283 | " | 100 | 0 |
| 284 | " | 90 | 0 |
| 285 | " | 95 | 0 |
| 286 | " | 100 | 0 |
| 287 | " | 90 | 0 |
| 288 | " | 100 | 0 |
| 289 | " | 100 | 0 |
| 290 | " | 100 | 0 |
| 291 | " | 100 | 0 |
| 292 | " | 100 | 0 |
| 293 | " | 100 | 0 |
| 294 | " | 100 | 0 |
| 295 | " | 100 | 0 |
| 296 | " | 100 | 0 |
| 297 | " | 100 | 0 |
| 298 | " | 100 | 0 |
| 299 | " | 100 | 0 |
| 300 | " | 100 | 0 |
| 301 | " | 100 | 0 |
| 302 | " | 100 | 0 |
| 303 | " | 100 | 0 |
| 304 | " | 100 | 0 |
| 305 | " | 100 | 0 |
| 306 | " | 100 | 0 |
| 307 | " | 100 | 0 |
| 308 | " | 100 | 0 |
| 309 | " | 100 | 0 |
| 310 | " | 100 | 0 |
| 311 | " | 100 | 0 |
| 312 | " | 100 | 0 |
| 313 | " | 100 | 0 |
| 314 | " | 100 | 0 |
| 315 | " | 100 | 0 |
| 316 | " | 100 | 0 |
| 317 | " | 100 | 0 |
| 318 | " | 100 | 0 |
| 319 | " | 100 | 0 |
| 320 | " | 100 | 0 |
| 321 | " | 100 | 0 |
| 322 | " | 100 | 0 |
| 323 | " | 100 | 0 |
| 324 | " | 100 | 0 |
| 325 | " | 100 | 0 |
| 326 | " | 100 | 0 |
| 327 | " | 100 | 0 |
| 328 | " | 100 | 0 |
| 329 | " | 100 | 0 |
| 330 | " | 100 | 0 |
| 331 | " | 100 | 0 |
| 332 | " | 100 | 0 |
| 333 | " | 100 | 0 |
| 334 | " | 100 | 0 |
| 335 | " | 100 | 0 |
| 336 | " | 100 | 0 |
| 337 | " | 100 | 0 |
| 338 | " | 100 | 0 |
| 339 | " | 100 | 0 |
| 340 | " | 100 | 0 |
| 341 | " | 100 | 0 |
| 342 | " | 100 | 0 |
| 343 | " | 100 | 0 |
| Comparative chemical (TPN) | " | 100 | 0 |
| Non-treated | — | 0 | — |

TEST EXAMPLE 7

Test for Control Effect on Cucumber Powdery Mildew

Over the first leaf stage seedlings of cucumber (variety: Sagami hanjiro) soil cultured in a porcelain pot of 9 cm in diameter in a greenhouse was sprayed 10 ml of a test solution of the compound diluted to a predetermined concentration. On the following day, the seedlings were inoculated by atomizing technique with a spore suspension of cucumber powdery mildew fungus (*Erysiphe cicholrcearum*). Ten days after the inoculation, percent lesion area (%) was investigated and the control value (%) was calculated according to the following equation.

$$\text{Preventive value (\%)} = \left(1 - \frac{\text{Percent lesion area in treated plot}}{\text{Percent lesion area in blank plot}}\right) \times 100$$

The results obtained are as shown in Table 8.

TABLE 8

| Compound No. | Concentration of spray liquid (ppm) | Control value (%) | Degree of phytotoxicity |
|---|---|---|---|
| 165 | 200 | 100 | 0 |
| 172 | " | 100 | 0 |
| 224 | " | 100 | 0 |
| 226 | " | 93 | 0 |
| 232 | " | 80 | 0 |
| 233 | " | 92 | 0 |
| 234 | " | 100 | 0 |
| 235 | " | 96 | 0 |
| 236 | " | 90 | 0 |
| 237 | " | 100 | 0 |
| 238 | " | 100 | 0 |
| 239 | " | 88 | 0 |
| 240 | " | 92 | 0 |
| 241 | " | 100 | 0 |
| 242 | " | 100 | 0 |
| 243 | " | 88 | 0 |
| 244 | " | 93 | 0 |
| 296 | " | 100 | 0 |
| 297 | " | 100 | 0 |
| 298 | " | 100 | 0 |
| Comparative chemical (Denmart) | 100 | 100 | 0 |
| Non-treated | — | 0 | — |

(Note)

Denmart: 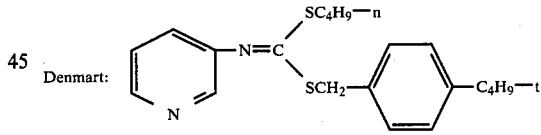

TEST EXAMPLE 8

Test for Control Effect on Pear Black Spot

The new shoots of pear (variety: Niju-seiki) was cut, leaving the developed leaves at the upper portion and then inserted into a 100 ml flask filled with 50 ml of water. Over the new shoots thus treated was sprayed 20 ml per two shoots a test liquid of the compound diluted to a predetermined concentration. On the following day, the shoots were inoculated by atomizing technique with a spore suspension of a pear alternaria leaf spot fungus (*Alternaria kikuchiana*), the spore concentration of which had been adjusted to become 50–60 spores per unit visible field under a microscope (Olympus) of 150 magnifications. After the inoculation, the shoots were kept in a humidified chamber at 25° C., and three days thereafter percent lesion area of each treated leaf was investigated and the control value (%) was calculated according to the following equation. Furthermore, the phytotoxicity against the pear tree of the test compound was investigated according to the same procedure as in Test Example 1. The results obtained are as shown in Table 9.

$$\text{Control value (\%)} = \left(1 - \frac{\text{Percent lesion area in treated plot}}{\text{Percent lesion area in blank plot}}\right) \times 100$$

TABLE 9

| Compound No. | Concentration of spray liquid (ppm) | Control value (%) | Degree of phytotoxicity |
|---|---|---|---|
| 207 | 500 | 92 | 0 |
| 208 | " | 78 | 0 |
| 210 | " | 100 | 0 |
| 211 | " | 100 | 0 |
| 212 | " | 100 | 0 |
| 213 | " | 92 | 0 |
| Comparative chemical (Captan) | " | 90 | 0 |
| Non-treated | — | 0 | — |

(Note)
Captan:

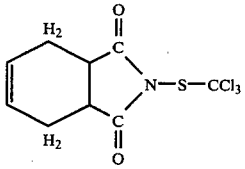

TEST EXAMPLE 9

Test for Seed Treatment against "Bakanae" Disease of Rice

Artificially inoculated rice seeds were obtained by inoculating a concentrated spore suspension of *Gibberella fujikuroi* causing the "Bakanae" disease at the ear-sprouting stage of a rice plant, and the rice seeds thus obtained were subjected to seed selection with water and then air dried to prepare rice seeds to be used in the test. The test compounds used were prepared according to the general procedure of Example 25. The test rice seeds each weight 15 g, were put in a saran net bag. The seed disinfection was conducted by immersing the unhulled rice-containing saran net bag at 15° C. for 24 hours in a test liquid, the proportion by volume of the test liquid and the infected rice seeds being 1:1. After completion of the disinfection, the rice seeds were subjected to preimmersion at 15° C. for 4 days, followed by germination acceleration treatment at 30° C. for 24 hours. The rice seeds thus treated were densely seeded in granular cultivation soil according to a standard seedling box method and then placed in a room kept at 30° C. for 2 days, followed by cultivation in a plastic greenhouse, exercising necessary supervision. Thirty two (32) days after the seeding (the 5-leaf stage), the number of seedlings infected with rice "Bakanae" disease (elongated and dead seedlings) was visually investigated to obtain the infected seedling ratio, and the seed disinfection ratio was calculated according to the following equation.

$$\text{Seed disinfection ratio (\%)} = \left(1 - \frac{\text{Infected seedling ratio in treated plot}}{\text{Infected seedling ratio in blank plot}}\right) \times 100$$

The results obtained are as shown in Table 10.

TABLE 10

| Compound No. | Concentration (ppm) | Seed disinfection ratio (%) | Degree of phytotoxicity |
|---|---|---|---|
| 1 | 1000 | 79 | 0 |
| 2 | " | 100 | 0 |
| 3 | " | 100 | 0 |
| 4 | " | 100 | 0 |
| 5 | " | 100 | 0 |
| 6 | " | 100 | 0 |
| 7 | " | 100 | 0 |
| 8 | " | 100 | 0 |
| 9 | " | 75 | 0 |
| 10 | " | 100 | 0 |
| 11 | " | 75 | 0 |
| 15 | " | 96 | 0 |
| 16 | " | 75 | 0 |
| 17 | " | 100 | 0 |
| 18 | " | 100 | 0 |
| 19 | " | 100 | 0 |
| 20 | " | 100 | 0 |
| 21 | " | 96 | 0 |
| 22 | " | 97 | 0 |
| 23 | " | 100 | 0 |
| 24 | " | 100 | 0 |
| 25 | " | 100 | 0 |
| 26 | " | 75 | 0 |
| 27 | " | 100 | 0 |
| 29 | " | 100 | 0 |
| 30 | " | 100 | 0 |
| 33 | " | 75 | 0 |
| 35 | " | 82 | 0 |
| 36 | " | 75 | 0 |
| 40 | " | 75 | 0 |
| 46 | " | 75 | 0 |
| 49 | " | 100 | 0 |
| 50 | " | 100 | 0 |
| 51 | " | 100 | 0 |
| 52 | " | 100 | 0 |
| 53 | " | 100 | 0 |
| 54 | " | 100 | 0 |
| 55 | " | 100 | 0 |
| 56 | " | 100 | 0 |
| 57 | " | 100 | 0 |
| 58 | " | 100 | 0 |
| 59 | " | 100 | 0 |
| 60 | " | 100 | 0 |
| 61 | " | 100 | 0 |
| 62 | " | 100 | 0 |
| 63 | " | 100 | 0 |
| 64 | " | 100 | 0 |
| 65 | " | 100 | 0 |
| 66 | " | 84 | 0 |
| 67 | " | 75 | 0 |
| 68 | " | 100 | 0 |
| 69 | " | 100 | 0 |
| 70 | " | 100 | 0 |
| 71 | " | 100 | 0 |
| 72 | " | 88 | 0 |
| 73 | " | 75 | 0 |
| 74 | " | 100 | 0 |
| 75 | " | 100 | 0 |
| 76 | " | 100 | 0 |
| 77 | " | 100 | 0 |
| 81 | " | 82 | 0 |
| 83 | " | 75 | 0 |
| 84 | " | 87 | 0 |
| 96 | " | 89 | 0 |
| 104 | " | 75 | 0 |
| 106 | " | 75 | 0 |
| 109 | " | 76 | 0 |
| 113 | " | 100 | 0 |
| 114 | " | 100 | 0 |

TABLE 10-continued

| Compound No. | Concentration (ppm) | Seed disinfection ratio (%) | Degree of phytotoxicity |
|---|---|---|---|
| 115 | " | 100 | 0 |
| 116 | " | 100 | 0 |
| 117 | " | 90 | 0 |
| 118 | " | 100 | 0 |
| 119 | " | 100 | 0 |
| 120 | " | 100 | 0 |
| 121 | " | 90 | 0 |
| 122 | " | 100 | 0 |
| 123 | " | 100 | 0 |
| 124 | " | 100 | 0 |
| 125 | " | 100 | 0 |
| 126 | " | 100 | 0 |
| 127 | " | 95 | 0 |
| 128 | " | 100 | 0 |
| 129 | " | 100 | 0 |
| 130 | " | 100 | 0 |
| 131 | " | 100 | 0 |
| 132 | " | 100 | 0 |
| 133 | " | 100 | 0 |
| 134 | " | 85 | 0 |
| 135 | " | 100 | 0 |
| 136 | " | 90 | 0 |
| 137 | " | 100 | 0 |
| 138 | " | 100 | 0 |
| 139 | " | 100 | 0 |
| 140 | " | 100 | 0 |
| 141 | " | 100 | 0 |
| 142 | " | 100 | 0 |
| 143 | " | 100 | 0 |
| 144 | " | 80 | 0 |
| 145 | " | 100 | 0 |
| 146 | " | 100 | 0 |
| 147 | " | 95 | 0 |
| 148 | " | 100 | 0 |
| 149 | " | 100 | 0 |
| 150 | " | 100 | 0 |
| 151 | " | 90 | 0 |
| 152 | " | 100 | 0 |
| 153 | " | 85 | 0 |
| 154 | " | 100 | 0 |
| 155 | " | 100 | 0 |
| 156 | " | 75 | 0 |
| 157 | " | 100 | 0 |
| 158 | " | 100 | 0 |
| 205 | " | 75 | 0 |
| 207 | " | 100 | 0 |
| 208 | " | 100 | 0 |
| 209 | " | 100 | 0 |
| 212 | " | 75 | 0 |
| 213 | " | 100 | 0 |
| 214 | " | 100 | 0 |
| 216 | " | 93 | 0 |
| 217 | " | 100 | 0 |
| 218 | " | 100 | 0 |
| 219 | " | 100 | 0 |
| 220 | " | 95 | 0 |
| 221 | " | 100 | 0 |
| 222 | " | 100 | 0 |
| 223 | " | 100 | 0 |
| 224 | " | 100 | 0 |
| 225 | " | 100 | 0 |
| 226 | " | 100 | 0 |
| 227 | " | 100 | 0 |
| 228 | " | 100 | 0 |
| 229 | " | 100 | 0 |
| 230 | " | 90 | 0 |
| 231 | " | 100 | 0 |
| 232 | " | 96 | 0 |
| 233 | " | 100 | 0 |
| 234 | " | 100 | 0 |
| 235 | " | 100 | 0 |
| 236 | " | 92 | 0 |
| 237 | " | 100 | 0 |
| 238 | " | 93 | 0 |
| 239 | " | 97 | 0 |
| 240 | " | 100 | 0 |
| 241 | " | 100 | 0 |
| 242 | " | 100 | 0 |
| 243 | " | 90 | 0 |
| 244 | " | 100 | 0 |
| 245 | " | 100 | 0 |
| 246 | " | 100 | 0 |
| 247 | " | 100 | 0 |
| 248 | " | 100 | 0 |
| 249 | " | 100 | 0 |
| 252 | " | 100 | 0 |
| 253 | " | 100 | 0 |
| 254 | " | 90 | 0 |
| 260 | " | 95 | 0 |
| 262 | " | 100 | 0 |
| 263 | " | 100 | 0 |
| 264 | " | 100 | 0 |
| 265 | " | 100 | 0 |
| 266 | " | 100 | 0 |
| 267 | " | 100 | 0 |
| 268 | " | 100 | 0 |
| 269 | " | 100 | 0 |
| 270 | " | 100 | 0 |
| 271 | " | 100 | 0 |
| 272 | " | 100 | 0 |
| 273 | " | 100 | 0 |
| 274 | " | 100 | 0 |
| 275 | " | 100 | 0 |
| 276 | " | 100 | 0 |
| 277 | " | 100 | 0 |
| 278 | " | 100 | 0 |
| 279 | " | 100 | 0 |
| 280 | " | 100 | 0 |
| 281 | " | 100 | 0 |
| 282 | " | 100 | 0 |
| 283 | " | 100 | 0 |
| 284 | " | 100 | 0 |
| 285 | " | 100 | 0 |
| 286 | " | 100 | 0 |
| 287 | " | 100 | 0 |
| 288 | " | 100 | 0 |
| 289 | " | 100 | 0 |
| 290 | " | 100 | 0 |
| 294 | " | 77 | 0 |
| 299 | " | 100 | 0 |
| Comparative chemical (Benomyl) | " | 95 | 0 |
| Non-treated | — | 0 | — |

(Note)
Benomyl:

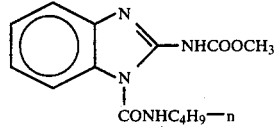

TEST EXAMPLE 10

Test for Seed Treatment against Brown Spot of Rice

The test was conducted in the same manner as in Test Example 9 and using the test compounds prepared according to Example 6, except that rice seeds (variety: Asominori) naturally infected with a rice brown spot fungus were used as the test seed rice. Twenty five (25) days after the seeding (the 3rd-leaf stage), the number of infected seedlings was visually investigated to obtain the infected seedling ratio and thereby to calculate the seed disinfection ratio (%) according to the following equation.

$$\text{Seed disinfection ratio (\%)} = \left(1 - \frac{\text{Infected seedling ratio in treated plot}}{\text{Infected seedling ratio in blank plot}}\right) \times 100$$

The results obtained are as shown in Table 11.

TABLE 11

| Compound No. | Concentration (ppm) | Seed disinfection ratio (%) | Degree of phytotoxicity |
|---|---|---|---|
| 2 | 1000 | 100 | 0 |
| 3 | " | 100 | 0 |
| 4 | " | 100 | 0 |
| 5 | " | 100 | 0 |
| 7 | " | 100 | 0 |
| 10 | " | 100 | 0 |
| 18 | " | 100 | 0 |
| 20 | " | 100 | 0 |
| 22 | " | 100 | 0 |
| 23 | " | 100 | 0 |
| 24 | " | 100 | 0 |
| 30 | " | 100 | 0 |
| 50 | " | 100 | 0 |
| 51 | " | 100 | 0 |
| 52 | " | 100 | 0 |
| 57 | " | 100 | 0 |
| 58 | " | 100 | 0 |
| 59 | " | 100 | 0 |
| 63 | " | 100 | 0 |
| 64 | " | 100 | 0 |
| 65 | " | 100 | 0 |
| 69 | " | 100 | 0 |
| 143 | " | 100 | 0 |
| 146 | " | 100 | 0 |
| 147 | " | 100 | 0 |
| 148 | " | 100 | 0 |
| 149 | " | 100 | 0 |
| 205 | " | 96 | 0 |
| 207 | " | 96 | 0 |
| 208 | " | 97 | 0 |
| 213 | " | 94 | 0 |
| 215 | " | 100 | 0 |
| 216 | " | 100 | 0 |
| 217 | " | 99 | 0 |
| 218 | " | 98 | 0 |
| 221 | " | 92 | 0 |
| 222 | " | 100 | 0 |
| 223 | " | 100 | 0 |
| 224 | " | 100 | 0 |
| 225 | " | 100 | 0 |
| 226 | " | 100 | 0 |
| 231 | " | 100 | 0 |
| 232 | " | 100 | 0 |
| 233 | " | 95 | 0 |
| 234 | " | 100 | 0 |
| 235 | " | 100 | 0 |
| 236 | " | 95 | 0 |
| 237 | " | 100 | 0 |
| 238 | " | 100 | 0 |
| 239 | " | 100 | 0 |
| 240 | " | 96 | 0 |
| 241 | " | 97 | 0 |
| 242 | " | 100 | 0 |
| 243 | " | 100 | 0 |
| 244 | " | 100 | 0 |
| Comparative chemical (TMTD) | " | 51 | 0 |
| Non-treated | — | 0 | — |

(Note)
TMTD: $(CH_3)_2NCSSCN(CH_3)_2$ (with S=C double bonds)

TEST EXAMPLE 11

Test for Antifungal Activity against Various Pathogenic Fungi Causing Plant Diseases The test compound is dissolved in acetone, and 1 ml of the solution and 20 ml of a medium (PSA medium pH 5.8) kept at about 60° C. are mixed together in a 9 cm diameter petri dish to prepare a compound-containing agar plate having a predetermined concentration. After evaporating the acetone while removing the upper cover of the Shale overnight, the compound-containing agar plate medium is inoculated by means of platinum loop with a spore suspension of the test fungus previously cultured in a slant medium. After culturing at 24° C. for 48 hours, the growth of the test fungus was investigated according to the following standard for determining the growth of fungus. The results obtained are as shown in Tables 12a and 12b.

Standard for determining the growth of fungus:
—: No growth of the fungus is recognized at all.
⊥: Formation of only few colonies is observed at the portion where the spore suspension has been applied to, while the growth of the fungus is markedly prohibited.
+: Formation of many colonies is observed at the portion where the spore suspension has been applied to, but the whole surface of the applied portion is not covered yet by colonies, and the growth of the fungus is markedly prohibited.
++: The growth of the fungus is observed practically all over the surface of the applied portion, but the degree of the growth of the fungus is moderately poor.
+++: The growth of the fungus is observed all over the surface of the applied portion, and the fungus normally grows.

TABLE 12a

| Compound No. | Conc. (ppm) | Fusarium oxysporum f. cucumerinum | Cladosporium fulvum | Glomerella cingulata | Alternaria kikuchiana | Pyricularia oryzae | Cochliobolus miyabeanus | Valsa mali |
|---|---|---|---|---|---|---|---|---|
| 1 | 50 | ⊥~+ | — | ⊥ | — | — | — | —~⊥ |
| 2 | " | — | — | — | — | — | — | — |
| 3 | " | — | — | — | — | — | — | — |
| 4 | " | — | — | — | — | — | — | — |
| 5 | " | + | + | — | ⊥ | — | — | + |
| 6 | " | + | ++ | ⊥ | — | — | — | ++ |
| 7 | " | — | — | — | — | — | — | — |
| 8 | " | —~⊥ | — | — | — | — | — | ⊥~+ |
| 10 | " | — | ⊥~+ | — | — | — | — | ± |
| 15 | " | ± | ++ | ⊥~+ | ⊥ | — | — | ± |
| 17 | " | — | ⊥~— | — | — | — | — | — |
| 18 | " | ± | + | — | — | — | — | ⊥~+ |
| 19 | " | —~⊥ | + | — | — | — | — | ⊥~+ |

TABLE 12a-continued

| Compound No. | Conc. (ppm) | Fusarium oxysporum f. cucumerinum | Cladosporium fulvum | Glomerella cingulata | Alternaria kikuchiana | Pyricularia oryzae | Cochliobolus miyabeanus | Valsa mali |
|---|---|---|---|---|---|---|---|---|
| 20 | " | ⊥ | + | − | − | − | − | ⊥~+ |
| 21 | " | + | ⊥~+ | − | − | − | − | ⊥~+ |
| 22 | " | − | − | − | − | − | − | − |
| 23 | " | ⊥ | −~⊥ | − | − | − | − | + |
| 24 | " | − | − | − | − | − | − | − |
| 25 | " | + | +~++ | + | + | − | ⊥ | + |
| 26 | " | + | ++ | ± | ⊥~+ | − | − | + |
| 27 | " | − | − | − | − | − | − | ± |
| 29 | " | + | + | − | ⊥~+ | − | − | + |
| 30 | " | + | + | − | − | − | − | + |
| 31 | " | + | ++ | ⊥ | + | − | − | + |
| 32 | " | + | ++ | + | ⊥~+ | − | − | + |
| 35 | " | + | + | + | ⊥~+ | − | − | ++ |
| 49 | " | ⊥~+ | − | − | −~⊥ | − | − | ⊥ |
| 50 | " | − | − | − | − | − | − | ± |
| 51 | " | − | − | − | − | − | − | − |
| 52 | " | − | − | − | − | − | − | − |
| 53 | " | ⊥ | ⊥ | − | − | − | − | ⊥~+ |
| 54 | " | ⊥ | − | − | − | − | − | + |
| 55 | " | − | − | − | − | − | − | − |
| 56 | " | + | ⊥ | − | ⊥ | − | − | +~++ |
| 57 | " | − | ⊥ | − | − | − | − | − |
| 58 | " | − | − | − | − | − | − | ⊥ |
| 59 | " | − | − | − | − | − | − | − |
| 60 | " | −~+ | −~+ | −~⊥ | −~⊥ | − | − | −~+ |
| 61 | " | ⊥~+ | − | − | − | − | − | + |
| 62 | " | + | + | − | −~⊥ | − | − | +~++ |
| 63 | " | − | ⊥ | − | − | − | − | − |
| 64 | " | − | − | − | − | − | − | ⊥~+ |
| 65 | " | − | − | − | − | − | − | − |
| 66 | " | +~++ | ⊥~+ | − | − | − | − | + |
| 67 | " | + | ± | − | − | − | − | + |
| 68 | " | + | + | − | ⊥~+ | − | − | +~++ |
| 69 | " | − | ⊥ | − | − | − | − | − |
| 70 | " | ⊥~+ | −~+ | − | − | − | − | ⊥~+ |
| 71 | " | − | − | − | − | − | − | − |
| 72 | " | + | + | −~⊥ | − | − | − | + |
| 73 | " | ⊥~+ | − | − | − | − | − | + |
| 74 | " | +~++ | ⊥~+ | − | − | − | − | +~++ |
| 75 | " | ⊥~++ | ⊥~+ | −~⊥ | − | − | − | ⊥~+ |
| 76 | " | − | − | − | − | − | − | ⊥~+ |
| 77 | " | − | − | − | − | − | − | − |
| 78 | " | ⊥~++ | ⊥~+ | −~⊥ | −~⊥ | − | ⊥~+ | +~++ |
| 79 | " | + | + | ⊥ | −~+ | − | − | + |
| 84 | " | ++ | ++ | + | + | − | − | + |
| 85 | " | + | ++ | −~⊥ | +~++ | − | − | ++ |
| 86 | " | + | ++ | ⊥~+ | ⊥ | − | − | + |
| 96 | " | − | − | − | − | − | − | − |

TABLE 12b

| Compound No. | Conc. (ppm) | Gibberella Fujikuroi | Cladosporium fulvum | Glomerella cingulata | Alternaria kikuchiana | Pyricularia oryzae | Cochliobolus miyabeanus | Valsa mali |
|---|---|---|---|---|---|---|---|---|
| 113 | 20 | − | ⊥ | ⊥ | − | − | − | + |
| 114 | " | − | + | ⊥ | − | − | − | ++ |
| 115 | " | − | −~⊥ | ⊥ | − | − | − | ⊥ |
| 116 | " | − | ⊥ | ⊥ | − | − | − | + |
| 117 | " | + | ++ | ++ | ++ | − | +~++ | ++ |
| 118 | " | − | − | − | − | − | − | −~+ |
| 119 | " | − | ⊥ | ⊥ | − | − | − | ⊥ |
| 120 | " | − | ⊥ | ⊥ | − | − | − | ⊥ |
| 122 | " | ⊥ | ++ | ⊥ | ⊥ | − | − | ++ |
| 123 | " | ⊥~+ | ++ | ⊥ | + | − | ⊥ | + |
| 124 | " | − | + | ⊥ | − | − | − | + |
| 125 | " | − | + | − | ⊥ | − | − | + |
| 126 | " | ⊥ | + | ⊥ | ⊥~+ | − | − | + |
| 127 | " | + | ++ | + | ++ | − | − | + |
| 128 | " | − | + | + | − | − | − | + |
| 129 | " | − | + | ⊥~+ | − | − | − | + |
| 130 | " | ++ | ++ | ++ | ++ | − | + | ++ |
| 131 | " | − | ⊥ | ⊥ | − | − | − | + |
| 132 | " | − | + | ⊥~++ | − | − | − | + |
| 133 | " | − | ++ | ⊥ | − | − | − | + |
| 134 | " | + | + | + | +~++ | − | − | ++ |
| 135 | " | ++ | + | + | ++ | − | − | + |
| 136 | " | ++ | + | ++ | ++ | − | ⊥ | ++ |
| 137 | " | − | + | ⊥ | ⊥ | − | − | + |

TABLE 12b-continued

| Compound No. | Conc. (ppm) | Gibberella Fujikuroi | Cladosporium fulvum | Glomerella cingulata | Alternaria kikuchiana | Pyricularia oryzae | Cochliobolus miyabeanus | Valsa mali |
|---|---|---|---|---|---|---|---|---|
| 138 | " | ++ | ++ | + | ++ | +~++ | ++ | ++ |
| 139 | " | − | ⊥ | ⊥ | − | − | − | ⊥ |
| 140 | " | − | ⊥ | ⊥ | − | − | − | ⊥ |
| 141 | " | − | ⊥ | ⊥ | − | − | − | + |
| 142 | " | − | ⊥ | ⊥ | − | − | − | ⊥ |
| 144 | " | ⊥ | ⊥~+ | ⊥ | ⊥ | − | − | ++ |
| 145 | " | − | − | − | − | − | − | ++ |
| 146 | " | ++ | ⊥~+ | ⊥ | ⊥~+ | − | − | ++ |
| 147 | " | ++ | + | ⊥ | ++ | − | − | ++ |
| 148 | " | ++ | + | − | ++ | − | − | ++ |
| 149 | " | ++ | ⊥~+ | − | ++ | − | − | ++ |
| 151 | " | ++ | +~++ | − | ++ | − | − | ++ |
| 155 | " | ⊥ | ⊥ | ⊥ | ⊥ | − | − | ++ |
| 156 | " | ++ | ++ | ++ | ++ | − | − | ++ |
| 157 | " | ++ | ++ | ++ | ++ | − | − | ++ |
| 158 | " | + | ++ | ⊥ | ++ | − | − | ++ |
| 246 | " | − | − | − | − | − | − | − |
| 247 | " | − | ⊥ | ⊥ | − | − | − | − |
| 248 | " | + | + | + | − | − | − | + |
| 249 | " | − | + | ⊥ | − | − | − | + |
| 252 | " | − | ⊥ | − | − | − | − | ⊥ |
| 253 | " | + | ++ | + | + | − | − | ++ |
| 256 | " | ⊥ | + | + | − | − | − | + |
| 257 | " | ⊥ | + | + | ⊥ | − | − | + |
| 258 | " | ⊥ | + | + | ⊥ | − | − | + |
| 259 | " | + | + | + | + | − | − | + |
| 260 | " | − | ⊥ | − | − | − | − | + |
| 262 | " | − | ⊥ | ⊥ | ⊥ | − | ⊥ | + |
| 263 | " | − | ⊥ | ⊥ | ⊥ | ⊥ | ⊥ | + |
| 264 | " | + | − | ⊥ | − | − | ⊥ | ⊥ |
| 265 | " | + | + | + | + | − | − | + |
| 267 | " | + | + | + | ⊥ | − | − | + |
| 269 | " | ++ | + | + | + | − | − | + |
| 270 | " | ⊥ | ⊥ | ⊥ | ⊥ | − | − | + |
| 271 | " | + | + | + | + | − | − | + |
| 273 | " | + | ++ | + | + | − | − | + |
| 274 | " | − | ⊥ | ⊥ | − | − | − | + |
| 275 | " | ⊥ | + | + | − | − | − | + |
| 276 | " | − | + | + | + | − | − | + |
| 280 | " | + | ⊥ | + | ++ | ⊥ | + | + |
| 281 | " | + | ⊥ | − | + | − | − | ++ |
| 282 | " | ⊥ | ⊥ | ⊥ | + | ⊥ | ⊥ | + |
| 283 | " | − | − | − | − | − | − | ⊥ |
| 284 | " | ⊥ | ⊥ | + | + | ⊥ | − | + |
| 285 | " | + | + | + | + | ⊥ | − | + |
| 286 | " | ⊥ | ⊥ | − | − | ⊥ | ⊥ | ⊥ |
| 288 | " | ⊥ | ⊥ | + | ⊥ | − | − | + |
| 289 | " | + | + | + | + | ⊥ | − | + |
| 291 | " | ⊥ | + | ⊥ | − | − | − | + |
| 294 | " | − | + | − | − | − | − | + |
| 295 | " | − | + | ⊥ | − | − | − | + |
| 297 | " | + | + | + | − | − | − | + |
| 298 | " | − | ++ | ⊥ | − | − | − | + |
| 300 | " | − | + | ⊥ | − | − | − | + |
| 301 | " | − | − | ⊥ | − | − | − | ⊥ |
| 303 | " | + | + | + | ++ | − | − | + |
| 304 | " | + | ⊥ | − | + | − | − | ⊥ |
| 305 | " | − | ⊥ | − | − | − | − | ⊥ |
| 306 | " | − | − | − | − | − | − | + |
| 307 | " | − | ⊥ | − | − | − | − | + |
| 308 | " | − | − | − | − | − | − | ⊥ |
| 309 | " | − | + | + | − | + | − | − |
| 310 | " | − | + | + | ⊥ | − | − | + |
| 311 | " | + | + | ⊥ | ⊥ | − | ⊥ | + |
| 312 | " | − | ⊥ | − | − | − | − | + |
| 313 | " | ⊥ | ⊥ | ⊥ | ⊥ | − | − | + |
| 314 | " | − | ⊥ | − | − | − | − | + |
| 315 | " | ⊥ | + | ⊥ | ⊥ | − | − | + |
| 316 | " | − | ⊥ | − | − | − | − | + |
| 317 | " | − | + | − | − | − | − | + |
| 318 | " | ⊥ | + | − | − | − | − | + |
| 319 | " | − | ⊥ | − | − | − | − | + |
| 320 | " | − | ⊥ | − | − | − | − | + |
| 322 | " | + | + | ⊥ | − | − | − | + |
| 323 | " | − | ⊥ | − | − | − | − | + |
| 324 | " | ⊥ | + | ⊥ | − | − | − | + |
| 325 | " | + | + | − | + | − | − | + |
| 326 | " | ⊥ | ⊥ | ⊥ | ⊥ | − | − | + |
| 327 | " | − | ⊥ | − | − | − | − | + |
| 328 | " | ⊥ | ⊥ | − | − | − | − | + |

-continued

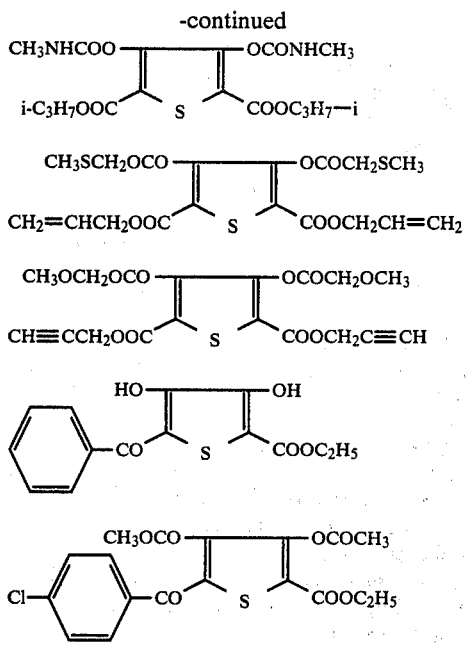

4. A compound according to claim 1, which is

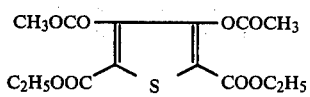

5. A fungicide for agricultural and horticultural purposes, characterized by containing as its active ingredient a thiophene derivative represented by the general formula

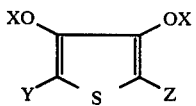

wherein X represents hydrogen atom, alkalimetal, —NH$_4$, —COR$_1$ (in which R$_1$ represents phenyl, halophenyl, lower alkyl, lower alkenyl, lower alkoxy lower alkyl, lower alkylthio lower alkyl, lower haloalkyl,

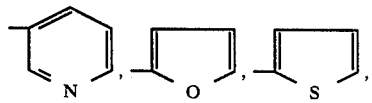

cycloalkyl or lower alkylthio), —CO-lower alkyl-R$_2$ (in which R$_2$ represents lower alkylcarbonyloxy or lower alkoxycarbonyl),

(in which n represents an integer of 4 to 6 inclusive), di-lower alkylcarbamoyl, mono-lower alkylcarbamoyl, cycloalkylcarbamoyl, —COOR$_3$ (in which R$_3$ represents lower alkyl, lower alkenyl, lower alkynyl, lower haloalkyl, lower alkoxy lower alkyl, lower alkoxycarbonyl lower alkyl, phenyl, substituted phenyl or benzyl), —SO$_2$R$_4$ (in which R$_4$ represents lower alkyl, lower alkyl-substituted phenyl or di-lower alkylamino) or

(in which R$_5$ represents lower alkyl); Y represents —COOR$_6$ (in which R$_6$ represents alkyl, lower alkenyl, lower alkynyl, lower alkoxy lower alkyl, or benzyl), hydrogen atom or

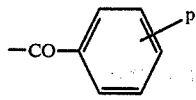

(in which p represents hydrogen atom, halogen atom or lower alkyl); and Z represents COOR$_6$ (in which R$_6$ is as defined above), cyano or

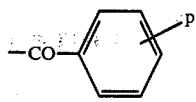

(in which p is as defined above), provided that both Y and Z are not —COOR$_6$ (in which R$_6$ represents alkyl, lower alkyl or lower alkynyl) when X represents hydrogen atom, alkali metal or —NH$_4$.

6. A fungicide according to claim 5, wherein the thiophene derivative is of the general formula defined before wherein X is taken as a group —COR$_1$ (in which R$_1$ is lower alkyl, lower alkoxy lower alkyl, or lower alkylthio lower alkyl), a group —COOR$_3$ (in which R$_3$ is lower alkyl) or mono-lower alkylcarbamoyl; Y is taken as a group —COOR$_6$ (in which R$_6$ is lower alkyl, lower alkenyl or lower alkynyl) or a group

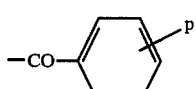

(in which p is hydrogen or halogen); and Z is taken as a group —COOR$_6$ as defined above.

7. A fungicide according to claim 5, wherein said thiophene derivative is one member selected from:

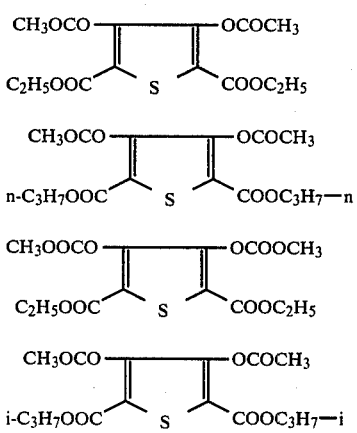

-continued

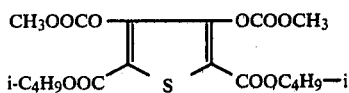

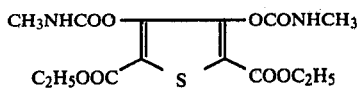

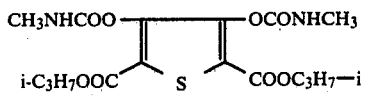

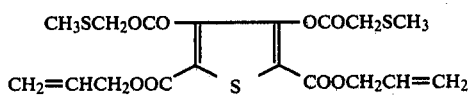

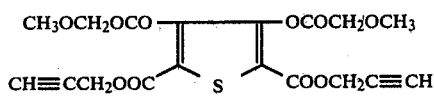

-continued

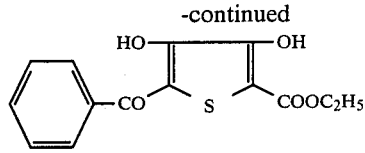

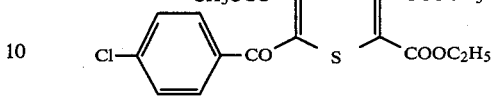

8. A fungicide as claimed in any one of claims 5 to 7, wherein said thiophene derivative is present in the amount of 0.1 to 80% by weight based on the total formulation.

9. A fungicide as claimed in claim 8, wherein the form of the formulation is a dust and the content of the thiophene derivative is 0.1 to 5% by weight.

10. A fungicide as claimed in claim 8, wherein the formulation is in the form of granules and the content of the thiophene derivative is 5 to 20% by weight.

11. A fungicide as claimed in claim 8, wherein the formulation is in the form of wettable powder and the content of the thiophene derivative is 0.1 to 5% by weight.

12. A fungicide as claimed in claim 8, wherein the formulation is in the form of emulsifiable concentrate and the content of the thiophene derivative is 10 to 40% by weight.

* * * * *